(12) United States Patent
Holmeide

(10) Patent No.: US 8,178,708 B2
(45) Date of Patent: May 15, 2012

(54) LIPID DERIVATIVES

(75) Inventor: Anne Kristin Holmeide, Oslo (NO)

(73) Assignee: Pronova Biopharma Norge AS, Lysaker (NO)

( * ) Notice: Subject to any disclaimer, the term of this patent is extended or adjusted under 35 U.S.C. 154(b) by 309 days.

(21) Appl. No.: 12/293,966

(22) PCT Filed: Mar. 23, 2007

(86) PCT No.: PCT/IB2007/000731
§ 371 (c)(1),
(2), (4) Date: Sep. 22, 2008

(87) PCT Pub. No.: WO2007/107869
PCT Pub. Date: Sep. 27, 2007

(65) Prior Publication Data
US 2009/0105499 A1    Apr. 23, 2009

(30) Foreign Application Priority Data
Mar. 23, 2006    (GB) ................................ 0605900.0

(51) Int. Cl.
*A23D 9/00* (2006.01)
*A61K 31/00* (2006.01)
*A61K 31/45* (2006.01)

(52) U.S. Cl. ........ 554/224; 554/227; 514/506; 514/724; 514/613; 562/598; 560/128; 560/205

(58) Field of Classification Search .................. None
See application file for complete search history.

(56) References Cited

U.S. PATENT DOCUMENTS
4,264,517 A * 4/1981 Liang ............................ 554/224
(Continued)

FOREIGN PATENT DOCUMENTS
DE        178298        7/1904
(Continued)

OTHER PUBLICATIONS

Christodoulopoulou, L. et al., Piperidinyl amides with insecticidal activity from the maritime plant Otanthus maritimus, 2005, Journal of Agricultural and Food Chemistry, vol. 53, pp. 1435-1439 (5 pages).*

(Continued)

*Primary Examiner* — Yate K Cutliff
(74) *Attorney, Agent, or Firm* — Finnegan, Henderson, Farabow, Garrett & Dunner, LLP

(57) ABSTRACT

The present invention relates to lipid compounds of the general formula (I): wherein -n=0-2, —$R_1$ and $R_2$ are the same or different and may be selected from a group of substituents consisting of a hydrogen atom, an alkyl group, a halogen atom, and an alkoxy group; -, X is $COR_3$ or $CH_2OR_4$, wherein —$R_3$ is selected from the group consisting of hydrogen, hydroxy, alkoxy, and amino, —wherein X further comprises carboxylic acid derivatives when $R_3$ is hydroxy and —$R_4$ is selected from the group consisting of hydrogen, alkyl or acyl, —Y is a $C_9$ to $C_{21}$ alkene with one or more double bonds with E or Z configuration; or any pharmaceutically acceptable complex, solvate or pro-drug thereof. The present invention also relates to pharmaceutical compositions comprising such lipid compounds, and to such lipid compounds for use as medicaments or for diagnostic purposes.

(I)

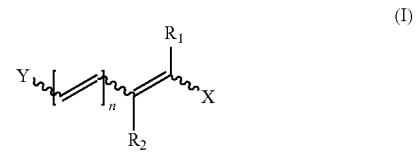

34 Claims, 1 Drawing Sheet

U937 3xκB-LUCcells were pre-incubated with 12.5 μM of substances/vehicle control in 18 hours prior to induction of NF-kB using LPS and TNFα. Luminescens was measured after 6 hours a show NF-κB activation.

U.S. PATENT DOCUMENTS 5,407,816 A 4/1995 Bringi et al.

FOREIGN PATENT DOCUMENTS

| GB | 2218904 | * 11/1989 |
| WO | WO 98/32444 | 7/1998 |
| WO | WO 03/095403 A1 | 11/2003 |
| WO | WO 2007/107869 A3 | 9/2007 |

OTHER PUBLICATIONS

Han, H., Targeted prodrug design to optimize drug delivery, 2000, AAPS, 2(1) article 6, (11 pages).*

L-DOPA Wikipedia, http://en.wikkpedia,org/wiki/levodopa, 2008, 5 pages.*

Prodrug, http://en.wikipedia.org/wiki/prodrug, 2 pages.*

Silverman, R. B., the organic chemistry of Drug Design and Drug Action, 1992, Academic Press, Chapter 2, abstract (20 pages).*

Flock, S. et al., Synthesis of some polyunsaturated sulfur- and oxygen-containing fatty acids related to eicosapentaenoic and docosahexaenoic acids, 1999, ACTA chemical Scandinavica. vol. 53, pp. 436-445.*

Holmeide, A.K. et al., Synthesis of some polyunsaturated trifluoromethyl ketones as potential phospholiapse A2 inhibitors, 2000, J. Chem. Soc., Perkins Trans. 1, pp. 2271-2276.*

Bohlmann, F. and Rotard, W., "Synthese von $(2E,4Z)$-2,4,11-Dodecatrien-1-al, einem Abbauprodukt der Linolensäure," *Liebigs Ann. Chem.* (1982) 1216-1219.

Bohlmann, F. et al., "Inhaltsstoffe aus *Gynoxys*- und Pseudogynoxys-Arten," *Phytochemistry* (1977) 16:774-776.

Flock, S. and Skattebøl, L., "Syntheses of three metabolites of icosapentaenoic and docosahaenoic acids," *J. Chem. Soc., Perkin Trans.* 1 (2000) 3071-3076.

Ghioni, C. et al., "Cultured Fish Cells Metabolize Octadecapentaenoic Acid (all-*cis* Δ3,6,9,12,15-18:5) to Octadecatetraenoic Acid (all-*cis* Δ6,9,12,15-18:4) via Its 2-*trans* Intermediate (*trans* Δ2, all-*cis* Δ6,9,12,15-18:5)," *Lipids* (2001) 36(2):145-152.

Granlund L. et al., "Effects of structural changes of fatty acids on lipid accumulation in adipocytes and primary hepatocytes," *Bichimica et Biophysica Acta* (2005) 1687:23-30.

Gunstone, F. et al., "Polyunsaturated acids, Part III Properties of the unsaturated aldehydes, acids and esters" Bangladesh Journal of Scientific and Industrial Research, (1978) 13(1-4): 169-172.

Hanley, K. et al., "Activators of the Nuclear Hormone Receptors PPARα and FXR Accelerate the Development of the Fetal Epidermal Permeability Barrier," *J. Clin. Invest.* (1997) 100(3):705-712.

Hopkins, C. Y. and Chisholm, M. J., "The Tetraenoic Acid of *Tecoma stans* Seed Oil," *J. Chem. Soc.* (1965) 907-910.

International Preliminary Report on Patentability for PCT/IB2007/000731 dated Jul. 28, 2008.

International Search Report for PCT/IB2007/000731 dated Sep. 7, 2007.

Lawrence, P. and Brenna, J. T., "Acetonitrile Covalent Adduct Chemical Ionization Mass Spectromety for Double Bond Localization in Non-Methylene-Interrupted Polyene Fatty Acid Methyl Esters," *Anal. Chem.* (2006) 78(4):1312-1317.

Luthria, D. L. et al., "Regulation of the Biosynthesis of 4,7,10,13,16,19-Docosahexaenoic Acid," *J. Biol. Chem.* (1996) 271(27):16020-16025.

Nagaki, M. et al., "Artificial Substrates of Medium-Chain Elongating Enzymes, Hexaprenyl- and Heptaprenyl Diphosphate Synthases," *Bioorg. & Med. Chem. Lett.* (2001) 11:2157-2159.

Ono, T. et al., "Reaction of α-(Phenylsulfinyl)acetonitrile with Aldehydes and Ketones to γ-Hydroxyalkenitriles and Syntheses of Terpenoids," *JACS* (1984) 106:7890-7893.

Sisson, T. M. et al., "Novel Polymer Architectures via the Selective Polymerization of Lyotropic Liquid Crystals of Heterobifunctional Amphiphiles," *JACS* (1998) 120:2322-2329.

Takahashi, N. et al., "Dual action of isoprenols from herbal medicines on both PPARγ and PPARα in 3T3-L1 adipocytes and HepG2 hepatocytes," *FEBS Letters* (2002) 514:315-322.

English Translation of DE 178298, 1904.

* cited by examiner

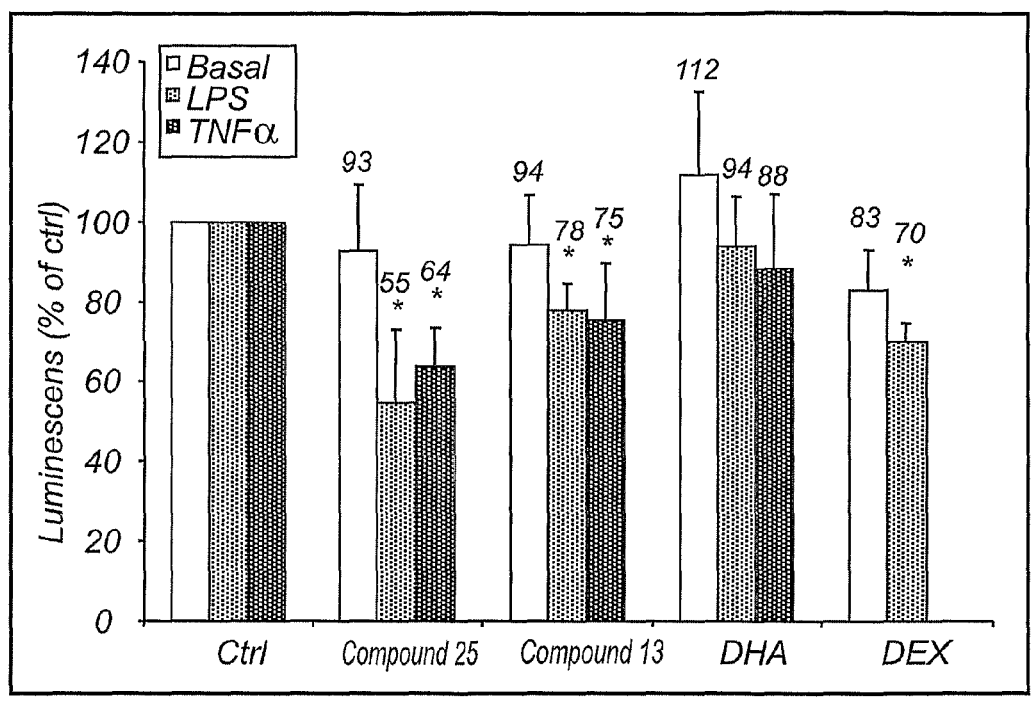
U937 3xκB-LUCcells were pre-incubated with 12.5 μM of substances/vehicle control in 18 hours prior to induction of NF-kB using LPS and TNFα. Luminescens was measured after 6 hours a show NF-κB activation.

LIPID DERIVATIVES

This application is a national stage filing under 35 U.S.C. §371 of International Application No. PCT/IB2007/000731, filed on Mar. 23, 2007, which claims the benefit of priority of British Application No. 0605900.0, filed on Mar. 23, 2006. The contents of each application are incorporated herein by reference.

TECHNICAL FIELD

The present invention relates to novel α,β-unsaturated fatty acid derivatives of unsaturated fatty acids, processes for preparing such compounds, pharmaceutical and lipid compositions containing such compounds and uses of such compounds and compositions in medicine.

BACKGROUND OF THE INVENTION

Dietary polyunsaturated fatty acids (PUFAs) have effects on diverse physiological processes impacting normal health and chronic diseases, such as the regulation of plasma lipid levels, cardiovascular and immune functions, insulin action, and neuronal development and visual function. Ingestion of PUFAs (generally in ester form, e.g. in glycerides or phospholipids) will lead to their distribution to virtually every cell in the body with effects on membrane composition and function, eicosanoid synthesis, cellular signalling and regulation of gene expression. Variations in distribution of different fatty acids/lipids to different tissues in addition to cell specific lipid metabolism, as well as the expression of fatty acid-regulated transcription factors, is likely to play an important role in determining how cells respond to changes in PUFA composition. (Benatti, P. Et al, J. Am. Coll. Nutr. 2004, 23, 281).

PUFAs or their metabolites have been shown to modulate gene transcription by interacting with several nuclear receptors. These are the peroxisome proliferators-activated receptors (PPARs), the hepatic nuclear receptor (HNF-4), liver X receptor (LXR), and the 9-cis retinoic acid receptor (retinoic X receptor, RXR). Treatment with PUFAs can also regulate the abundance of many transcriptional factors in the nucleus, including SREBP, NFκB, c/EBPβ, and HIF-1α. These effects are not due to direct binding of the fatty acid to the transcription factor, but involve mechanisms that affect the nuclear content of the transcription factors.

The regulation of gene transcription by PUFAs have profound effects on cell and tissue metabolism and offer a credible explanation for the involvement of nutrient-gene interactions in the initiation and prevention or amelioration of diseases such as obesity, diabetes, cardiovascular disorders, immune-inflammatory diseases and cancers (Wahle, J., et al, Proceedings of the Nutrition Society, 2003, 349).

Fish oils rich in the ω-3 polyunsaturated fatty acids eicosapentaenoic acid (EPA) and docosahexaenoic acid (DHA), have been shown to reduce the risk of cardiovascular diseases partly by reduction of blood triglyceride concentration. This favourable effect mainly results from the combined effects of inhibition of lipogenesis by decrease of SPEBP-1 and stimulation of fatty acid oxidation by activation of PPAR-α in the liver.

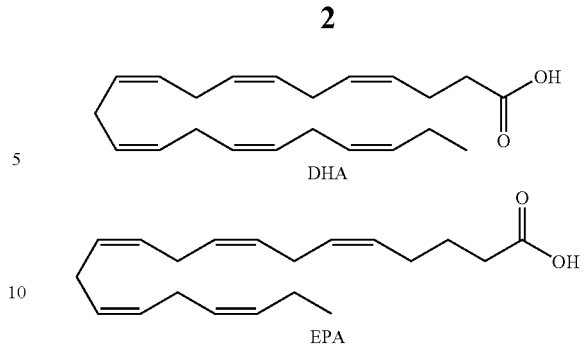

ω-3 polyunsaturated fatty acids in fish oil have been reported to improve the prognosis of several chronic inflammatory diseases characterized by leukocyte accumulation and leukocyte-mediated tissue injury, including atherosclerosis, IgA nephropathy, inflammatory bowel disease, rheumatoid arthritis, psoriasis, etc. (Mishra, A., Arterioscler. Thromb. Vasc. Biol., 2004, 1621).

DHA is the most abundant ω-3 PUFA in most tissues and it is highly enriched in neural membranes, constituting approximately 30-40% of the phospholipids of the grey matter of cerebral cortex and photoreceptor cells in the retina. DHA accumulates at high levels in the postnatal mammalian CNS indicating that DHA is involved in the maturation of the CNS. In several different species, decreased levels of DHA in the brain and retina are associated with impairments in neural and visual functions. DHA supplementation may be beneficial in treatment of depression, schizophrenia, hyperactivity, multiple sclerosis, Alzheimer, degenerative retinal diseases, and peroxisomal disorders. (Horrocks and Farooqui, Prostaglandins, Leukotrienes and Essential Fatty acids, 2004, 70, 361). Dietary DHA may also be beneficial in treatment of atherosclerosis, inflammation and cancer (Horrocks et al, Pharmacol Res 1999, 40: 211; Rose, et al, 1999, 83, 217).

Although ω-3 PUFAs possess many positive biological effects, their therapeutic value has been limited and the therapeutic area where the ω-3 PUFAs have been most promising is in the cardiovascular field as a triglyceride lowering agent. However, high doses of polyunsaturated fatty acids are necessary to cause hypolipidemia. One reason for this is degradation of the polyunsaturated fatty acids in liver by oxidation.

Nuclear receptors (NRs) constitute a large and high conserved family of ligand activated transcriptional factors that regulate diverse biological processes such as development, metabolism, and reproduction. It is recognised that ligands for these receptors might be used in the treatment of common diseases such as atherosclerosis, diabetes, obesity, and inflammatory diseases. As such, NRs have become important drug targets, and the identification of novel NR ligands is a subject of much interest. The activity of many nuclear receptors is controlled by the binding of small, lipophilic ligands that include hormones, metabolites such as fatty acids, bile acids, oxysteroles and xeno- and endobiotics. Nuclear receptors can bind as monomers, homodimers, or RXR heterodimers to DNA. Three types of heterodimeric complexes exist: unoccupied heterodimers, nonpermissive heterodimers that can be activated only by the partners ligand but not by an RXR ligand alone, and permissive heterodimers that can be activated by ligands of either RXR or its partner receptor and are synergistically activated in the presence of both ligands (Aranda and Pascual, Physiological Reviews, 2001, 81, 1269). As the obligate heterodimer partner for many nuclear receptors (including the vitamin D receptor (VDR), thyroid hormone receptor (TR), all-trans retinoic acid receptor (RAR), peroxisome proliferator-activated receptor (PPAR), liver-X receptor (LXR) and others) RXR plays the role of a master co-ordinator of multiple nuclear receptor pathways.

The ligands that regulate RXR heterodimer partners can roughly be divided into two subsets. One subset comprises high affinity, highly specific steroid/hormone ligands (VDR and TR) and act as endocrine modulators. The other subset binds to abundant, lower affinity lipid ligands (PPAR, LXR) and appears to act in part as lipid biosensors. The genes regulated by the RXR heterodimers include those involved in a wide variety of cellular processes including cell-cycle regulation and differentiation. They also regulate genes involved in lipid transport, biosynthesis, and metabolism (Goldstein, J. T. et al, Arch. Biochem and Biophys., 2003, 420, 185).

The cognate ligand of RXR is 9-cis-retinoic acid, a molecule that also binds and transactivates RAR with very similar affinity and efficiency. On the other hand all-trans-retinoic acid, the cognate ligand of RAR, does not bind to the RXR receptor.

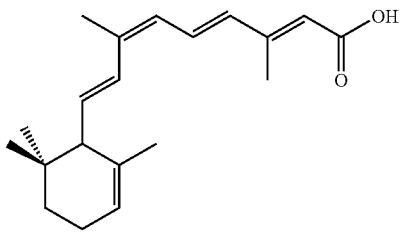

9-cis-Retinoic acid

Evidence has been provided that RXR ligands can function as insulin sensitizers and can decrease hyperglycaemia, hyperinsulinaemia and hypertriglyceridaemia in ob/ob and db/db mice (Mukherjee et al, Nature, 1997, 386, 407). It has also been published that chronic administration of RXR agonists to Zucker fa/fa rats reduces food intake and body weight gain, lowers plasma insulin concentrations while maintaining normoglycaemia (Liu, et al, Int. J. Obesity., 2000, 997; Ogilvie, K. et al, Endocrinology, 2004, 145, 565).

In 2000 it was published that DHA isolated from mice brain selectively activated RXR in cell-based assays (Urquiza et al, Science 2000, 290, 2140, WO 01/73439). In this study DHA did not activate RAR. Since then it has been published that several unsaturated fatty acids, including DHA, arachidonic acid, and oleic acid, have the capacity to specifically bind and activate the RXRα LBD (ligand binding domain) and thereby act as in vivo ligands for this receptor. (Lengquist J., et. al. Molecular & Cellular Proteomics 3, 2004, 692). In a study published by Fan et al, it was shown that DHA serve as a specific ligand for RXRα activation relative to n-6 PUFA in colonocytes (Carcinogenesis, 2003, 24, 1541).

Although RXR agonists are known and the compounds have been tested in different biological systems, the prior art does not describe the use of modified PUFAs as potent ligands for RXR.

The transcription factor NF-κB is an inducible eukaryotic transcription factor of the rel family. It is a major component of the stress cascade that regulate the activation of early response genes involved in the expression of inflammatory cytokines, adhesion molecules, heat-shock proteins, cyclooxygenases, lipoxygenases, and redox enzymes. Zhao, G. et al (Biochemical and Biophysical Research Comm., 2005, 909) suggest that the anti-inflammatory effects of PUFAs in human monocytic THP-1 cells are in part mediated by inhibition of NF-κB activation via PPAR-γ activation. Others have suggested that the anti-inflammatory effect of PUFAs is mediated through a PPAR-α dependent inhibition of NF-κB activation.

Receptor-selective ligands are a high priority in the search for NR-based drug leads, since native NR ligands present systemic side effects and toxicity due to their lack of binding specificity.

9-cis Retinoic acid regulates a wide variety of biological functions through a mechanism that entails binding to both RXR and RAR. These receptors are involved in many different functions. Their far reaching biological effects have motivated the search for RAR- or RXR-selective ligands. Non selective retinoid ligands when employed as drugs have side effects such as teratogenicity and mucocutaneously toxicity, which are significantly reduced when specific RXR agonists are used. Furthermore, it has been shown that tumour-specific apoptosis can be driven by RXR-selective agonists. Selective RXR agonists may offer an alternative approach for the treatment of metabolic disorders. There is thus a need for easily accessible RXR-selective ligands which may provide the above-mentioned benefits without the side effects of non-selective ligands.

Because many of the nuclear receptors are distributed differently in different tissues it is important to make ligands that in vivo are able to target specified cells in order to bind and activate the target receptor.

SUMMARY OF THE INVENTION

One object of the present invention is to provide lipid compounds having pharmaceutical activity.

This object is achieved by a lipid compound according to formula (I):

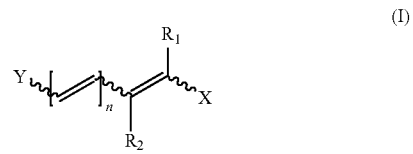

wherein n=0-2

$R_1$ and $R_2$ are the same or different and may be selected from a group of substituents consisting of a hydrogen atom, an alkyl group, a halogen atom, and an alkoxy group;

X is $COR_3$ or $CH_2OR_4$, wherein $R_3$ is selected from the group consisting of hydrogen, hydroxy, alkoxy, and amino, wherein X further comprises carboxylic acid derivatives when $R_3$ is hydroxy; and $R_4$ is selected from the group consisting of hydrogen, alkyl or acyl, Y is a $C_9$ to $C_{21}$ alkene with one or more double bonds with E- or Z configuration;

or any pharmaceutically acceptable complex, solvate or prodrug thereof.

In particular the present invention relates to lipid compounds with E-configuration according to formula (II):

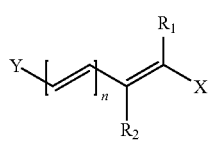
(II)

When X is represented by the formula $COR_3$ and $R_3$ is a hydroxy, the present invention also relates to derivatives of carboxylic acids. For example, such carboxylic acid derivatives may be selected from the group consisting of a phospholipid, or a mono-, di- or triglyceride.

In a lipid compound of the present invention, $R_1$ and $R_2$ in formula (I) are the same or different and may be selected from a group of substituents consisting of a hydrogen atom, a $C_1$-$C_7$ alkyl group, a $C_1$-$C_7$ alkoxy group, and a halogen atom.

Preferably, $R_1$ and $R_2$ are the same or different and are selected from a group of substituents consisting of a hydrogen atom, a $C_1$-$C_3$ alkyl group, a $C_1$-$C_3$ alkoxy group, and a halogen atom. More preferably, $R_1$ and $R_2$ are the same or different and are selected from a methyl group, an ethyl group, and a hydrogen atom.

When $R_1$ and/or $R_2$ is a halogen atom, it is preferably a fluorine atom. In a lipid compound of the present invention X may be represented by the formula $COR_3$. In such cases, $R_3$ may be a $C_1$-$C_7$-alkoxy group, or, more specifically, a $C_1$-$C_3$-alkoxy group. Alternatively, $R_3$ is a hydroxy group.

In alternative embodiments, X is represented by the formula $CH_2OR_4$. In such embodiments, $R_4$ may be a $C_1$-$C_7$-alkyl group, or, more specifically, a $C_1$-$C_3$-alkyl group. Alternatively, $R_4$ is a $C_1$-$C_7$ acyl group, especially a $C_1$-$C_3$ acyl group.

In a lipid compound according to the invention, the double bond between the carbon atoms 2 and 3 is preferably in E-configuration.

In embodiments of the present invention, wherein $R_1$ and $R_2$ are different and one is a $C_1$-$C_3$ alkoxy and the other one is a hydrogen, the double bond between the carbon atoms 2 and 3 may be in Z-configuration.

As specified in the general formula (I), Y may be a $C_9$ to $C_{21}$ alkene with one or more double bonds with E or Z configuration. In particular, Y is a $C_{14}$-$C_{19}$ alkene with 2-6 double bonds. In embodiments, Y is a $C_{14}$-$C_{19}$ alkene with 2-6 methylene interrupted double bonds in Z configuration. Alternatively, Y is unsubstituted. In preferred embodiments of the present invention, the lipid compound comprises a carbon-carbon double bond in the ω-3 position of Y.

Lipid compounds of the present invention may be categorized with regard to the number of conjugated systems, represented by the integer n of the bracket in formula (I) or (II). As specified, n may vary between 0 and 2.

When n=0, a lipid compound of the present invention relates to the formula (III):

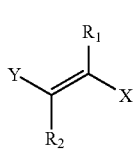
(III)

Further, lipid compounds represented by the formula (III) of the present invention may be subcategorized into the following preferred groups:

IIIa: X=$COR_3$
X=$COR_3$, wherein $R_3$ is a hydroxy group or a $C_1$-$C_3$ alkoxy group;
$R_1$ and $R_2$ are the same or different and are selected from a hydrogen atom, a $C_1$-$C_3$ alkyl group, a $C_1$-$C_3$ alkoxy group, and a halogen atom; and
Y is a $C_{13}$-$C_{19}$ alkene having 2-6 double bonds.

IIIb: X=$COR_3$, $R_1 \neq R_2$
X=$COR_3$, wherein $R_3$ is a hydroxy group or a $C_1$-$C_2$ alkoxy group;
$R_1$ and $R_2$ are different and one represents a hydrogen atom and the other one a $C_1$-$C_2$ alkyl group or a $C_1$-$C_2$ alkoxy group; and
Y is a $C_{17}$-$C_{19}$ alkene having 3-5 double bonds.

Preferred compounds of formula (III), and the subgroups IIIa or IIIb are the following lipid compounds 1-4, 6-8, and 26:

1:
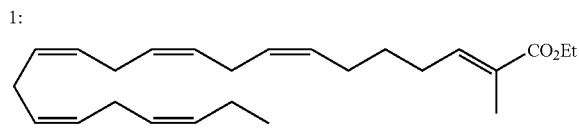

2:
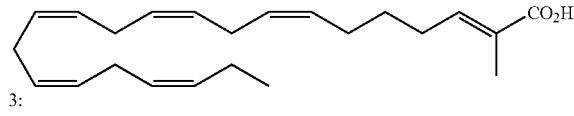

3:
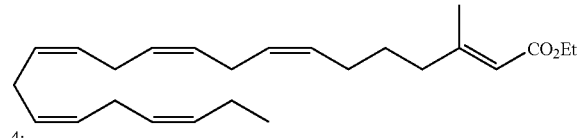

4:
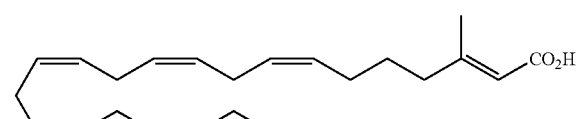

6:
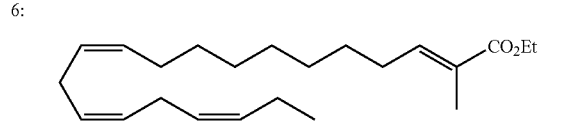

7:
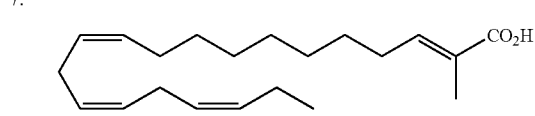

8:
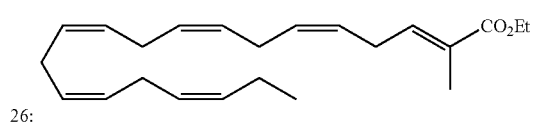

26:
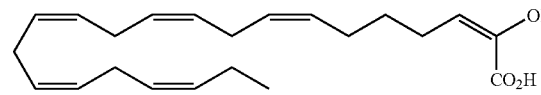

IIIc: X=$CH_2OR_4$
X=$CH_2OR_4$, wherein $R_4$ is hydrogen or a $C_1$-$C_3$ acyl group;

$R_1$ and $R_2$ are the same or different and are selected from a hydrogen atom, a $C_1$-$C_3$ alkyl group, a $C_1$-$C_3$ alkoxy group, and a halogen atom; and Y is a $C_{13}$-$C_{19}$ alkene having 2-6 double bonds.

IIId: X=$CH_2OR_4$, $R_1 \neq R_2$

X=$CH_2OR_4$, wherein $R_4$ is hydrogen; and $R_1$ and $R_2$ are different and one represents a hydrogen atom, and the other one a $C_1$-$C_2$ alkyl group or a $C_1$-$C_2$ alkoxy group;

Y is a $C_{17}$-$C_{19}$ alkene having 3-5 double bonds.

Preferred compounds of formula (III), and the subgroups IIIc and IIId are the following lipid compounds 5, 9, and 27:

5:

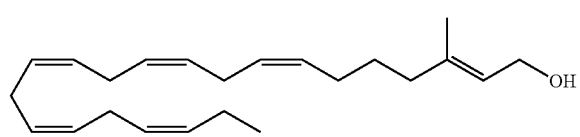

9:

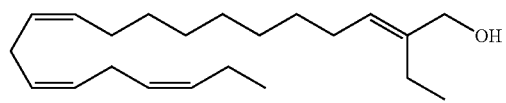

27:

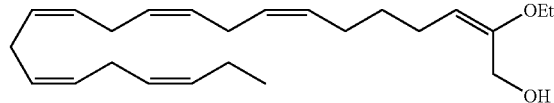

When n=1, a lipid compound of the present invention relates to the formula (IV):

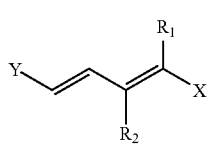

(IV)

Further, lipid compounds represented by the formula (IV) of the present invention may be subcategorized into the following preferred groups:

IVa: X=$COR_3$

X=$COR_3$, wherein $R_3$ is hydroxy group or a $C_1$-$C_3$ alkoxy group;

$R_1$ and $R_2$ are the same or different and are selected from a hydrogen atom, a $C_1$-$C_3$ alkyl group, and a halogen atom; and Y is a $C_{11}$-$C_{17}$ alkene having 2-6 double bonds.

IVb: X=$COR_3$, $R_1 \neq R_2$

X=$COR_3$, wherein $R_3$ is a hydroxy group or a $C_1$-$C_2$ alkoxy group; and $R_1$ and $R_2$ are different and one represents a hydrogen atom and the other one a $C_1$-$C_2$ alkyl group;

Y is a $C_{15}$-$C_{17}$ alkene having 3-5 double bonds.

Preferred compounds of formula (IV), and the subgroups IVa and IVb are the following lipid compounds 10-11, 17-18, 20, and 22.

10:

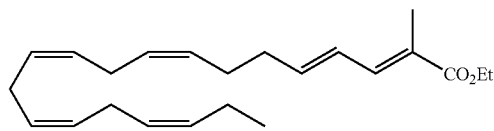

11:

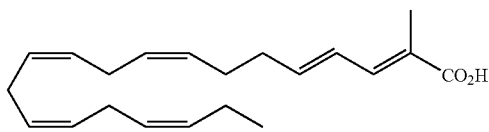

17:

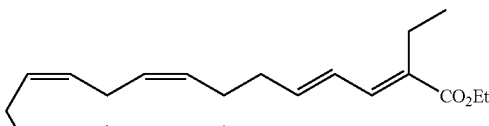

18:

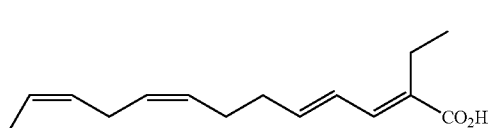

20:

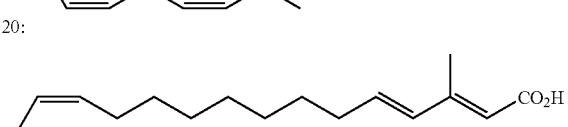

22:

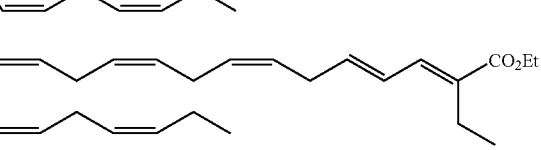

IVc: X=$COR_3$, $R_1=R_2$

X=$COR_3$, wherein $R_3$ is a hydroxy group or a $C_1$-$C_2$ alkoxy group;

$R_1$ and $R_2$ are hydrogen; and

Y is a $C_{11}$-$C_{17}$ alkene having 2-6 double bonds.

IVd: X=$COR_3$, $R_1=R_2$

X=$COR_3$, wherein $R_3$ is a hydroxy group or a $C_1$-$C_2$ alkoxy group;

$R_1$ and $R_2$ are hydrogen; and

Y is a $C_{15}$-$C_{17}$ alkene having 4-5 double bonds.

Preferred compounds of formula (IV), and the subgroups IVc and IVd are the following lipid compounds 12-15:

12:

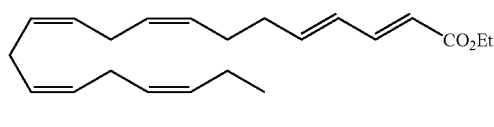

13:

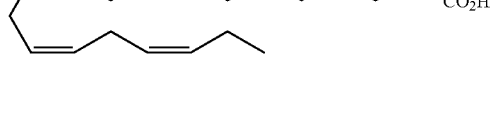

-continued

14:

[Structure: long polyene chain with CO₂Et terminus]

15:

[Structure: long polyene chain with CO₂H terminus]

IVe: X=CH₂OR₄
  X=CH₂OR₄, wherein R₄ is a hydrogen atom or a $C_1$-$C_3$ acyl group;
  $R_1$ and $R_2$ are the same or different and are selected from a hydrogen atom, a $C_1$-$C_3$ alkyl group, and a halogen atom; and
  Y is a $C_{11}$-$C_{17}$ alkene having 2-6 double bonds.

IVf: X=CH₂OR₄, $R_1 \neq R_2$
  X=CH₂OR₄, wherein R₄ is hydrogen;
  $R_1$ and $R_2$ are different and one represents a hydrogen atom and the other one a $C_1$-$C_2$ alkyl group; and
  Y is a $C_{15}$-$C_{17}$ alkene having 3-5 double bonds.

Preferred compounds of formula (IV), and the subgroups IVe and IVf are the following lipid compounds 19, 21, and 23:

19:

[Structure with OH terminus, ethyl branch]

21:

[Structure with OH terminus, methyl branch]

23:

[Structure with OH terminus, ethyl branch]

IVg: X=CH₂OR₄, $R_1 = R_2$
  X=CH₂OR₄, wherein R₄ is hydrogen;
  $R_1$ and $R_2$ are the same and represent hydrogen atoms; and
  Y is a $C_{11}$-$C_{17}$ alkene having 2-6 double bonds.

IVh: X=CH₂OR₄, $R_1 = R_2$
  X=CH₂OR₄, wherein R₄ is hydrogen;
  $R_1$ and $R_2$ are the same and represent hydrogen atoms; and
  Y is a $C_{17}$ alkene having 5 double bonds.

A preferred compound of formula (IV), and the subgroups IVg and IVh is the following lipid compound 16:

16:

[Structure with OH terminus]

When n=2, a lipid compound of the present invention relates to the formula (V):

$$\text{(V)}$$

[Structure showing Y—CH=CH—CH=CH—C(R₁)(R₂)—X with substituents]

Further, lipid compounds represented by the formula (V) of the present invention may be subcategorized into the following preferred groups:

Va: X=COR₃
  X=COR₃, wherein R₃ is a hydroxy group or a $C_1$-$C_3$ alkoxy group;
  $R_1$ and $R_2$ are the same or different and are selected from a hydrogen atom, a $C_1$-$C_3$ alkyl group, and a halogen atom; and
  Y is a $C_9$-$C_{16}$ alkene having 1-4 double bonds.

Vb: X=COR₃, $R_1 \neq R_2$
  X=COR₃, wherein R₃ is a hydroxy group or a $C_1$-$C_2$ alkoxy group;
  $R_1$ and $R_2$ are different and one represents a hydrogen atom and the other one a $C_1$-$C_2$ alkyl group; and
  Y is a $C_{15}$ alkene having 4 double bonds.

Preferred compounds of formula (V), and the subgroups Va and Vb are the following lipid compounds 24 and 25:

24:

[Structure with CO₂Et terminus, methyl branch]

25:

[Structure with CO₂H terminus, methyl branch]

The present invention also relates to a method for the production of a lipid compound according to any of the formulas (I)-(V) of the present invention.

Further, the present invention relates to a lipid compound according to any of the formulas (I)-(V) for use as a medicament or for diagnostic purposes, for instance positron emission tomography (PET).

The present invention also relates to a pharmaceutical composition comprising a lipid compound according to any of the general formulas (I)-(V). The pharmaceutical composition may comprise a pharmaceutically acceptable carrier, excipient or diluent, or any combination thereof, and is suitably formulated for oral administration. A suitable daily dosage of the lipid compound according to any of the formulas (I)-(V) is 5 mg to 10 g of said lipid compound; 50 mg to 1 g of said lipid compound, or 50 mg to 200 mg of said lipid compound.

The present invention also relates to lipid composition comprising a lipid compound according to any of the formulas (I)-(V). Suitably, at least 80% by weight, or at least 90% by weight, or at least 95% by weight of the lipid composition is comprised of said lipid compound. The lipid composition may further comprise a pharmaceutically acceptable antioxidant, e.g. tocopherol.

Further, the invention relates to the use of a lipid compound according to any of the formulas (I)-(V) for the production of a medicament for:

activation or modulation of at least one of the human peroxisome proliferator-activated receptor (PPAR) isoforms α, γ and/or δ;
activation or modulation of RXR;
inhibition or regulation of NF-κB;
treatment and/or the prevention of an inflammatory disease or condition;
reduction of plasma insulin, blood glucose and/or serum triglycerides;
prevention and/or treatment of elevated triglyceride levels, LDL cholesterol levels, and/or VLDL cholesterol levels;

Nomenclature and Terminology

Lipid compounds of the present invention are substituted at carbon 2 and/or 3 counted from the functional group, denoted X in the formulas (I)-(V). Such substitutions may be called an "alpha substitution" or a "beta substitution". In a lipid compound of the present invention, a double bond exists between the carbons 2 and 3, which preferably is in E-configuration.

As used herein, the term "ω-3 position" means that the first double bond exists as the third carbon-carbon bond from the terminal $CH_3$ end (ω) of the carbon chain.

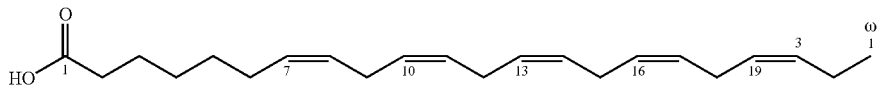

prevention and/or treatment of a hyperlipidemic condition, e.g. hypertriglyceridemia (HTG);
treatment and/or the prevention of obesity or an overweight condition;
treatment and/or the prevention of peripheral insulin resistance and/or a diabetic condition;
reduction of body weight and/or for preventing body weight gain;
treatment and/or the prevention of a fatty liver disease, e.g. non-alcoholic fatty liver disease (NAFLD);
treatment of insulin resistance, hyperlipidemia and/or obesity or an overweight condition; and
treatment and/or the prevention of type 2 diabetes.

The invention also relates to lipid compounds according to any of the formulas (I)-(V) for the treatment and/or prevention of the conditions listed above.

Furthermore, the invention relates to methods for the treatment and/or prevention of the conditions listed above, comprising administering to a mammal in need thereof a pharmaceutically active amount of a lipid compound according to any of the formulas (I)-(V).

DETAILED DESCRIPTION OF THE INVENTION

It has been surprisingly found that novel polyunsaturated derivatives represented by the general formula (I)-(V) have higher affinity for the nuclear receptors of the PPAR family compared to DHA and EPA. The derivatives provide more potent RXR agonists than DHA.

The RXR/PPAR is a permissive heterodimer that is synergistically activated in the presence of both ligands. Because the novel compounds of the present invention are ligands for both the PPARs and RXR they can act as dual acting agonists. Because different PUFAs accumulate differently in different tissues, these modified PUFAs have the potential for being tissue specific ligands for nuclear receptors.

In addition to being better ligands for the PPAR receptors and RXR, the derivatives of the invention are not as easily degraded by α- and β-oxidation pathways as natural PUFAs due to substituent in α- or β-position.

The novel compounds can be used either alone in therapy or in combination with other high affinity PPAR ligands. In this case the PUFA derivative will act as a RXR ligand to synergistically enhance the effect of the PPAR ligand on gene transcription.

In addition, novel compounds that adopt the functionality of the retinoids: retinol and retinal are provided. These compounds are pro-drugs that are activated in vivo by oxidation pathways.

In chemistry, the numbering of the carbon atoms starts from the α end. Fatty acids are straight chain hydrocarbons possessing a carboxyl (COOH) group at one end (α) and (usually) a methyl group at the other (ω) end.

As used herein, the expression "methylene interrupted double bonds" relates to the case when a methylene group is located between to separate double bonds in a carbon chain of lipid compound.

In a compound according to the invention, said alkyl group may be selected from the group consisting of methyl, ethyl, n-propyl, isopropyl, n-butyl, iso-butyl, sec.-butyl, and n-hexyl; said halogen atom may be fluorine; said alkoxy group may be selected from the group consisting of methoxy, ethoxy, propoxy, isopropoxy, sec.-butoxy, $OCH_2CF_3$, and $OCH_2CH_2OCH_3$;

Herein, said acyl group is compound of formula:

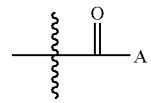

wherein A is a $C_1$-$C_7$ alkyl.

The basic idea of the present invention is a lipid compound of formula (I):

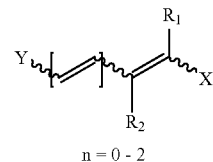

n = 0 - 2 wherein
$R_1$ and $R_2$ are the same or different and may be selected from a group of substituents consisting of a hydrogen atom, an alkyl group, a halogen atom, and an alkoxy group;
X is $COR_3$ or $CH_2OR_4$, wherein
$R_3$ is selected from the group consisting of hydrogen, hydroxy, alkoxy, and amino,
wherein X further comprises carboxylic acid derivatives when $R_3$ is hydroxy; and
$R_4$ is selected from the group consisting of hydrogen, alkyl or acyl, Y is a $C_9$ to $C_{21}$, alkene with one or more double bonds with E or Z configuration;

or any pharmaceutically acceptable complex, solvate or prodrug thereof.

Preferably, a lipid compound of the present invention is an E-isomer and is represented by the formula (II):

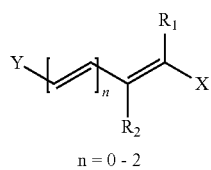

n = 0 - 2

When n=0, a lipid compound of the present invention is represented by the formula (III):

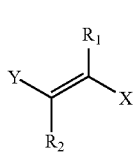

(III)

When n=1, a lipid compound of the present invention is represented by the formula (IV):

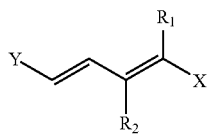

(IV)

When n=2, a lipid compound of the present invention is represented by the formula (V):

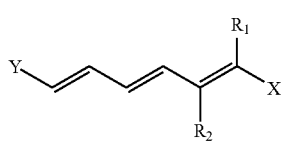

(V)

The compounds above may be subcategorized based on X being $COR_3$ or $CH_2OR_4$, the substituents $R_1$ and $R_2$, and whether $R_1$ and $R_2$ are different or the same, as well as the length and number of double bonds of the Y chain. Especially preferred compounds are the compounds (1)-(27) listed above.

Preferred lipid compounds according to the present invention may also be divided into the following categories A-1, A-2, B-1 and B-2.

Category A- Z- and/or E-Isomers

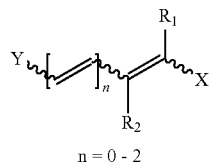

n = 0 - 2

General Formula (I)

The Z- and E-isomers of the compounds described by the general formula (I) can be separated from mixtures by different separation techniques. Flash chromatography (silica gel) is a common separation technique. The Z- and E-isomers of the compounds described by the general formula above can be separated in the form of carboxylic esters others as carboxylic acids or as alcohols by flash chromatography. The carboxylic acids can be re-esterified by the use of primary alcohols and an acidic catalyst ($H_2SO_4$, HCl, $BF_3$). The alcohols can be oxidized to give the carboxylic acid.

Category A-1, Z- and/or E-Isomers, n=0, X=$COR_3$

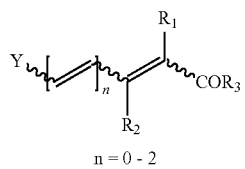

n = 0 - 2

For all examples within this category, (30), (32) and (33):

n=0

X=ethylcarboxylate

Ethyl (2Z/E,11E,14E,17E)-2-ethyl-eicosa-2,11,14,17-tetraenoate (30)

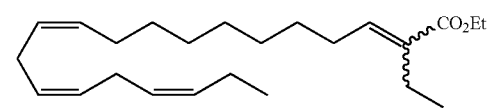

Ethyl (2Z/E,7Z,10Z,13Z,16Z,19Z)
2-ethoxy-docosa-2,7,10,13,16,19-hexaenoic acid
(32)

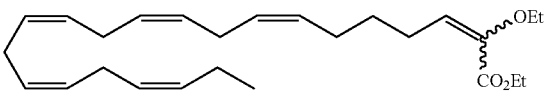

15

Ethyl (2Z,7Z,10Z,13Z,16Z,19Z) 2-ethoxy-docosa-2,7,10,13,16,19-hexaenoate acid (33)

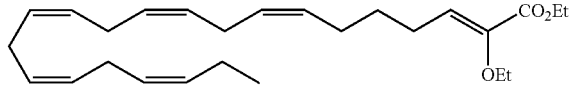

Category A-2, Z- and/or E-Isomers, n=0, X=CH$_2$OR$_4$

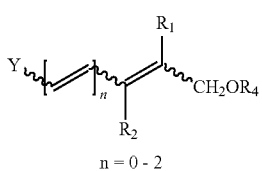

n = 0 - 2

For all examples within this category, (29), (31) and (34):
n=0
R$_4$=H (all-Z)-2-ethyl-eicosa-2,11,14,17-tetraen-1-ol (31)

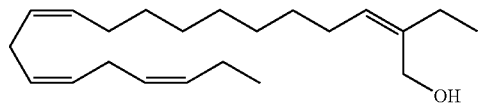

(all-Z)-3-methyl-docosa-2,7,10,13,16,19-hexaen-1-ol (29)

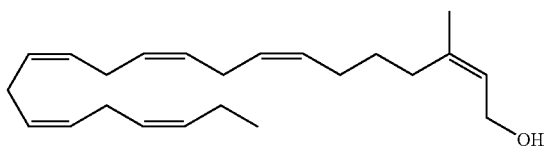

(all-Z)-2-ethoxy-docosa-2,7,10,13,16,19-hexaen-1-ol (34)

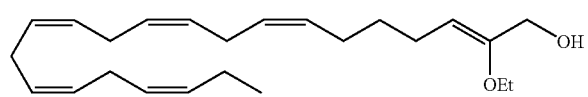

16

Category A-1, n=1, X=COR$_3$ and X=CH$_2$OR$_4$

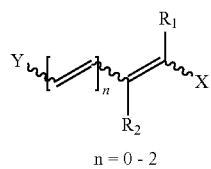

n = 0 - 2

For all examples within this category, (35), (36), (37), (38), (39) and (40):
n=1

Ethyl (2Z,4E,8Z,11Z,14Z,17Z)-2-ethyl-eicosa-2,4,8,11,14,17-hexaneoate (35)

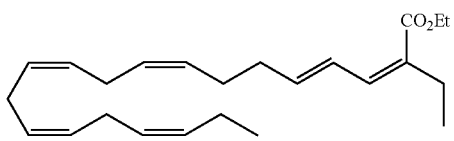

(2Z,4E,8Z,11Z,14Z,17Z)-2-ethyl-eicosa-2,4,8,11,14,17-hexaen-1-ol (36)

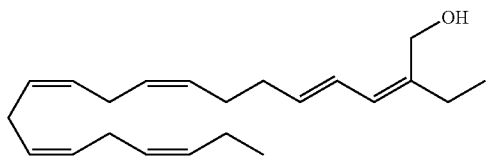

Ethyl (2E/Z,4E,13Z,16Z,19Z)-3-methyl-docosa-2,4,13,16,19-pentaenoate (37)

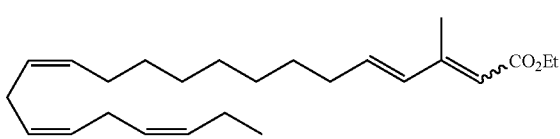

(2Z,4E,13Z,16Z,19Z)-3-methyl-docosa-2,4,13,16,19-pentaen-1-ol (38)

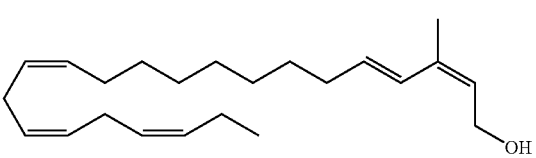

(2Z,4E,7Z,10Z,13Z,16Z,19Z)-2-ethyl-docosa-2,4,7,
10,13,16,19-heptaen-1-ol (39)

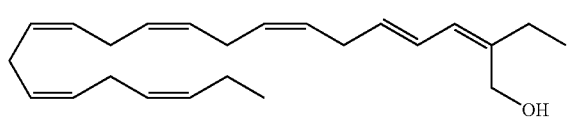

Ethyl(2Z/2E,4E,13Z,16Z,19Z)-2-ethyl-docosa-2,4,
13,16,19-heptaenoate (40)

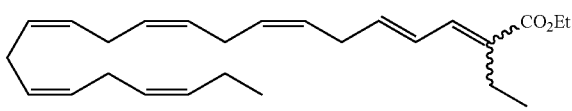

Category B: E-Isomers

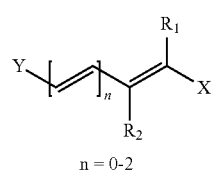

n = 0-2

General formula (II), wherein preferably
Y=$C_9$ to $C_{21}$ alkene with one or more double bonds with E- or Z-configuration.
X=hydroxymethyl (—$CH_2OH$), carbaldehyde (—C(O)H), or carboxylic acid or a derivative thereof, a carboxylate, carboxylic anhydride or carboxamide. $R_1$ and $R_2$, which may be the same or different each represent a hydrogen atom, a fluorine atom, an alkoxy group, or an alkyl group.
Category B-1: E-Isomers, n=0-2 and X=$COR_3$

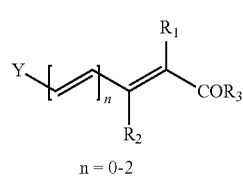

n = 0-2

Category B-2; E-Isomers, n=0-2 and X=$CH_2OR_4$

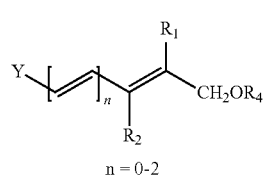

n = 0-2

Category B-1; n=0, X=$COR_3$ and $R_3$=$OCH_2CH_3$
For all examples within this category, (1), (3), (6) and (8):
n=0
X=ethylcarboxylate Ethyl (2E,7Z,10Z,13Z,16Z,19Z)-2-methyl-docosa-2,
7,10,13,16,19-hexaenoate (1)

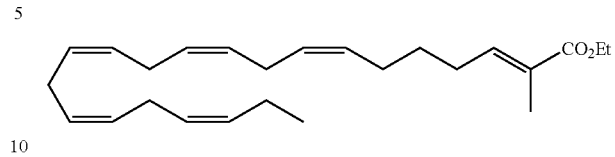

Ethyl (2E,7Z,10Z,13Z,16Z,19Z)-3-methyl-docosa-2,
7,10,13,16,19-hexaenoate (3)

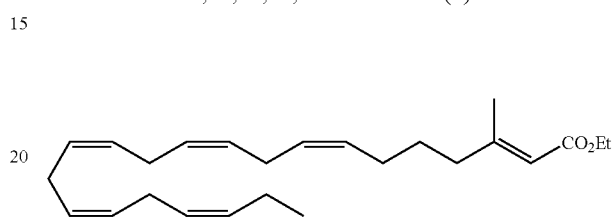

Ethyl (2E,11Z,14Z,17Z)-2-methyl-eicosa-2,11,14,
17-tetraenoate (6)

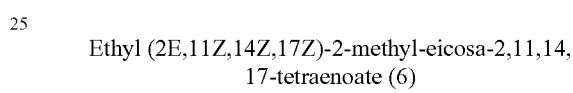

Ethyl (2E,5Z,8Z,11Z,14Z,17Z)-2-methyl-icosa-2,5,
8,11,14,17-hexaenoate (8)

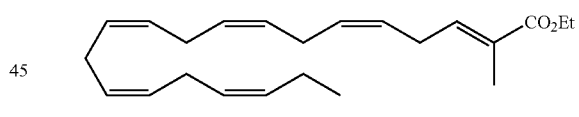

Category B-1; n=0, X=$COR_3$ and $R_3$=OH
For all examples within this category, (2), (4), (7) and (26):
n=0
$R_3$=hydroxy (OH)

(2E,7Z,10Z,13Z,16Z,19Z)-2-methyl-docosa-2,7,10,
13,16,19-hexaenoic acid (2)

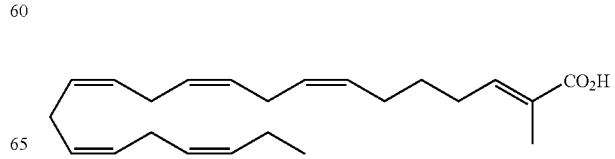

19

(2E,7Z,10Z,13Z,16Z,19Z)-3-methyl-docosa-2,7,10,13,16,19-hexaenoic acid (4)

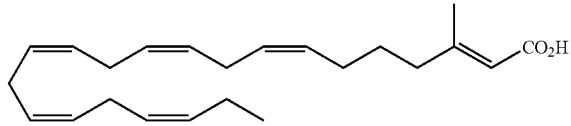

(2E,11E,14E,17E)-2-methyl-eicosa-2,11,14,17-tetraenoic acid (7)

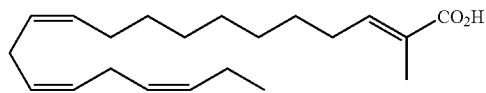

(2Z,7Z,10Z,13Z,16Z,19Z)
2-ethoxy-docosa-2,7,10,13,16,19-hexaenoic acid (26)

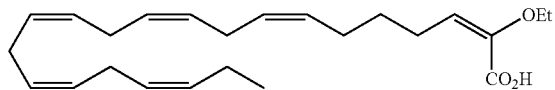

Category B-2, n=0, X=CH$_2$OR$_4$ and R$_4$=H

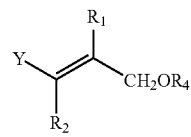

For all examples within this category; (5), (9) and (27):
n=0
The substituent is an alkyl or an ethoxy.

(2E,7Z,10Z,13Z,16Z,19Z)-3-methyl-docosa-2,7,10,13,16,19-hexaen-1-ol (5)

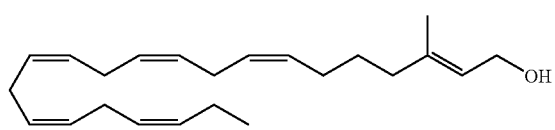

20

(2E,11Z,14Z,17Z)-2-ethyl-eicosa-2,11,14,17-tetraen-1-ol (9)

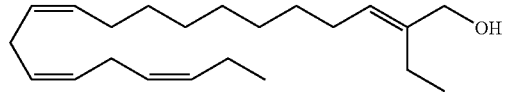

2E,7Z,10Z,13Z,16Z,19Z)-2-ethoxy-docosa-2,7,10,13,16,19-hexaen-1-ol (27)

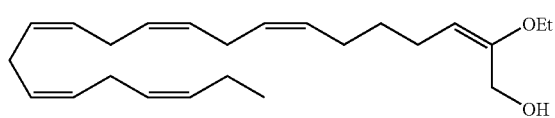

Category B-1, E-isomers, n=1

Formula (IV)

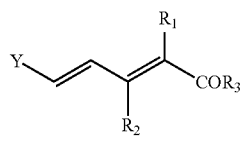

n = 1

Category B-1, n=1 and X=COR$_3$ and R$_3$=OCH$_2$CH$_{13}$

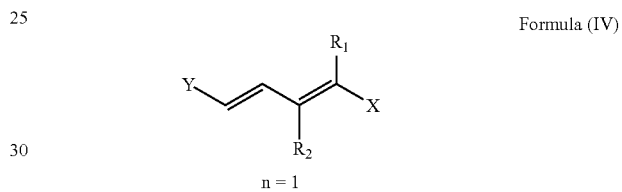

For all examples within this category, (10), (12), (14), (17) and (22):
n=1
X=COR$_3$
R$_3$=OCH$_2$CH$_3$ Ethyl (2E,4E,8Z,11Z,14Z,17Z)-2-methyl-icosa-2,4,8,11,14,17-hexaenoate (10)

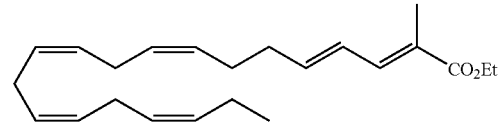

21

Ethyl (2E,4E,8Z,11Z,14Z,17Z)-icosa-2,4,8,11,14,17-hexaenoate (12)

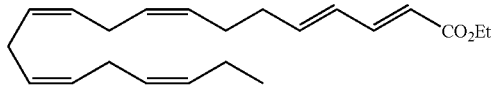

Ethyl (2E,4E,7Z,10Z,13Z,16Z,19Z)-docosa-2,4,7,10,13,16,19-heptaenoate (14)

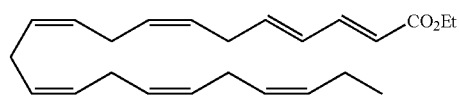

Ethyl-(2E,4E,8Z,11Z,14Z,17Z)-2-ethyl-eicosa-2,4,8,11,14,17-hexaneoate (17)

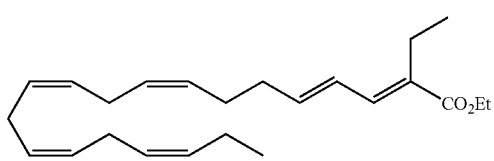

Ethyl (2E,4E,7Z,10Z,13Z,16Z,19Z)-2-ethyl-docosa-2,4,7,10,13,16,19-heptaenoate (22)

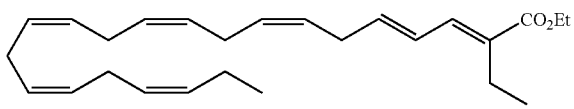

Category B-1, E-isomers, n=1 and X=COR$_3$ and R$_3$=OH

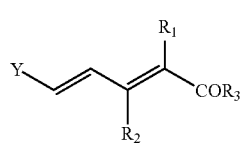

For all examples within this category, (11), (13), (15), (18) and (20):
n=1
X=COOH

22

(2E,4E,8Z,11Z,14Z,17Z)-2-methyl-icosa-2,4,8,11,14,17-hexaenoic acid (11)

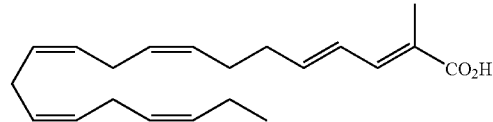

(2E,4E,8Z,11Z,14Z,17Z)-icosa-2,4,8,11,14,17-hexaenoic acid (13)

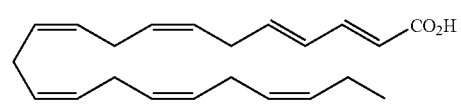

2E,4E,7Z,10Z,13Z,16Z,19Z)-docosa-2,4,7,10,13,16,19-heptaenoic acid (15)

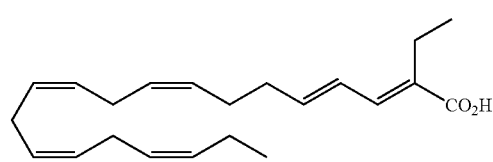

(2E,4E,8Z,11Z,14Z,17Z)-2-ethyl-icosa-2,4,8,11,14,17-hexaenoic acid (18)

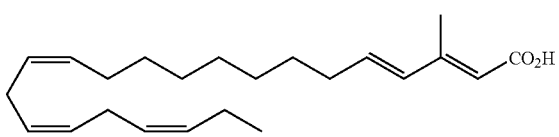

(2E,4E,13Z,16Z,19Z)-3-methyl-docosa-2,4,13,16,19-pentaenoic acid (20)

Category B-2, E-isomers, n=1, X=CH₂OR₄ and R₄=H

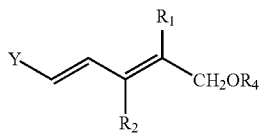

For all examples within this category, (16), (19), (21) and (23):
n=1
X=CH₂OR₄
R₄=Hydrogen (H)

(2E,4E,7Z,10Z,13Z,16Z,19Z)-docosa-2,4,7,10,13,16,19-heptaen-1-ol (16)

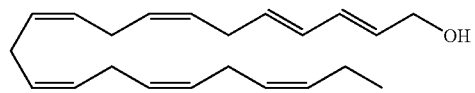

(2E,4E,8Z,11Z,14Z,17Z)-2-ethyl-icosa-2,4,11,14,17-hexaen-1-ol (19)

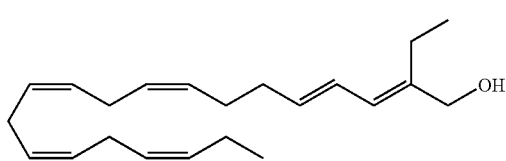

(2E,4E,13Z,16Z,19Z)-3-methyl-docosa-2,4,13,16,19-pentaen-1-ol (21)

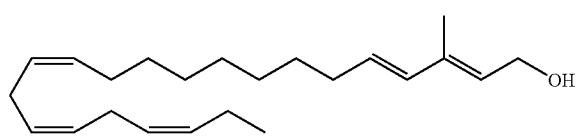

(2E,4E7Z,10Z,13Z,16Z,19Z)-2-ethyl-docosa-2,4,7,10,13,16,19-heptaen-1-ol (23)

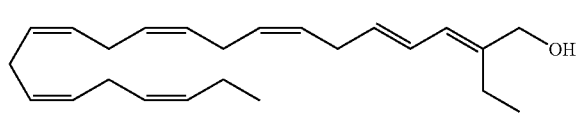

Category B, Trans isomers, n=2

Formula (V)

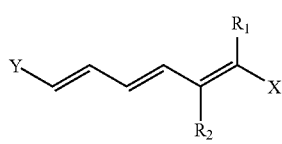

n = 2

Category B-1, n=2, X=COR₃ and R₃=OCH₂CH₃

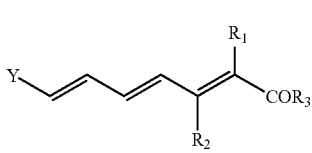

For the example within this category (24);
n=2
X=COR₃
R₃=OCH₂CH₃

Ethyl (2E,4E,6E,10Z,13Z,16Z,19Z)-3-methyl-docosa-2,4,6,10,13,16,19-heptaenoate (24)

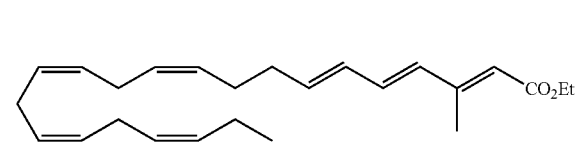

Category B-1, n=2, X=COR₃ and R₃=OH

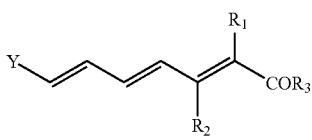

For the example within this category (25);
n=2
X=COR₃
R₃=hydroxyl (OH)

(2E,4E,6E,10Z,13Z,16Z,19Z)-3-methyl-docosa-2,4,6,10,13,16,19-heptaenoic acid (25)

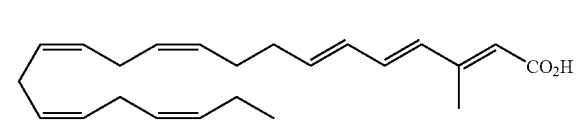

It is to be understood that the present invention encompasses any possible pharmaceutically acceptable complexes, solvates or prodrugs of the lipid compounds of the formulas (I)-(V).

"Prodrugs" are entities which may or may not possess pharmacological activity as such, but may be administered (such as orally or parenterally) and thereafter subjected to bioactivation (for example metabolization) in the body to form the agent of the present invention which is pharmacologically active.

Where X is a carboxylic acid, the present invention also includes derivatives of carboxylic acids. For example, such carboxylic acid derivatives may be selected from the group consisting of a phospholipid, or a mono-, di- or triglyceride.

Furthermore, salts of carboxylic acids are also included in the present invention. Suitable pharmaceutically acceptable salts of carboxy groups includes metal salts, such as for example aluminium, alkali metal salts such as lithium, sodium or potassium, alkaline metal salts such as calcium or magnesium and ammonium or substituted ammonium salts.

A "pharmaceutically active amount" relates to an amount that will lead to the desired pharmacological and/or therapeutic effects, i.e. an amount of the lipid compound which is effective to achieve its intended purpose. While individual patient needs may vary, determination of optimal ranges for effective amounts of the lipid compound is within the skill of the art. Generally, the dosage regimen for treating a condition with the compounds and/or compositions of this invention is selected in accordance with a variety of factors, including the type, age, weight, sex, diet and medical condition of the patient.

By "a medicament" is meant a lipid compound according to any of the formulas (I)-(V), in any form suitable to be used for a medical purpose, e.g. in the form of a medicinal product, a pharmaceutical preparation or product, a dietary product, a food stuff or a food supplement.

"Treatment" includes any therapeutic application that can benefit a human or non-human mammal. Both human and veterinary treatments are within the scope of the present invention. Treatment may be in respect of an existing condition or it may be prophylactic.

The lipid compounds of the formulas (I)-(V) may be used on their own but will generally be administered in the form of a pharmaceutical composition in which the compounds of formulas (I)-(V) (the active ingredient) are in association with a pharmaceutically acceptable carrier, excipient or diluent (including combinations thereof).

Acceptable carriers, excipients and diluents for therapeutic use are well known in the pharmaceutical art, and can be selected with regard to the intended route of administration and standard pharmaceutical practice. Examples encompass binders, lubricants, suspending agents, coating agents, solubilising agents, preserving agents, wetting agents, emulsifiers, sweeteners, colourants, flavouring agents, odourants, buffers, suspending agents, stabilising agents, and/or salts.

A pharmaceutical composition according to the invention is preferably formulated for oral administration to a human or an animal. The pharmaceutical composition may also be formulated for administration through any other route where the active ingredients may be efficiently absorbed and utilized, e.g. intravenously, subcutaneously, intramuscularly, intranasally, rectally, vaginally or topically.

In a specific embodiment of the invention, the pharmaceutical composition is shaped in form of a capsule, which could also be a microcapsule generating a powder or a sachet. The capsule may be flavoured. This embodiment also includes a capsule wherein both the capsule and the encapsulated composition according to the invention is flavoured. By flavouring the capsule it becomes more attractive to the user. For the above-mentioned therapeutic uses the dosage administered will, of course, vary with the compound employed, the mode of administration, the treatment desired and the disorder indicated.

The pharmaceutical composition may be formulated to provide a daily dosage of e.g. 5 mg to 10 g; 50 mg to 1 g; or 50 mg to 200 g of the lipid compound. By a daily dosage is meant the dosage per 24 hours.

The dosage administered will, of course, vary with the compound employed, the mode of administration, the treatment desired and the disorder indicated. Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The lipid compound and/or the pharmaceutical composition of the present invention may be administered in accordance with a regimen of from 1 to 10 times per day, such as once or twice per day. For oral and parenteral administration to human patients, the daily dosage level of the agent may be in single or divided doses.

A further aspect of the present invention relates to a lipid composition comprising a lipid compound of any of the formulas (I)-(V). The lipid composition may comprise in the range of 80 to 100% by weight of the lipid compound of the formulas (I)-(V), all percentages by weight being based on the total weight of the lipid composition. For example, at least 80%, at least 90%, or at least 95% by weight of the lipid composition is comprised of lipid compounds of any of the formulas (I)-(V).

In specific embodiments of the invention, the lipid composition is a pharmaceutical composition, a nutritional composition or a dietary composition.

The lipid composition may further comprise an effective amount of a pharmaceutically acceptable antioxidant, e.g tocopherol or a mixture of tocopherols, in an amount of up to 4 mg per g, e.g. 0.05 to 0.4 mg per g, of tocopherols, of the total weight of the lipid composition.

The lipid compounds and compositions according to the invention are useful for the treatment of a wide range of diseases and conditions, as will be described in more detail below.

Suitably, lipid compounds according to any of the formulas (I)-(V) may activate the nuclear receptors PPAR (peroxisome proliferator-activated receptor) isoforms α and/or γ and/or δ, as well as RXR.

Furthermore, lipid compounds according to the invention may regulate or inhibit NFκB (nuclear factor kappa B) activity.

Especially preferred compounds for inhibition and/or regulation of NFκB are those of the formulas (IV) and (V), i.e. the lipid compounds represented by n=1 or n=2. Preferably, $R_1$ is represented by a hydrogen atom.

The present invention also provides the use of a lipid compound according to any of the formulas (I)-(V) for the manufacture of a medicament for the treatment/and or prevention of an inflammatory disease or condition.

Especially preferred compounds for treatment/and or prevention of an inflammatory disease or condition are those of the formulas (IV) and (V), i.e. the lipid compounds represented by n=1 or n=2. Preferably, $R_1$ is represented by a hydrogen atom.

In a further aspect, the present invention relates to the use of a lipid compound according to any of the formulas (I)-(V) for the manufacture of a medicament for the reduction of plasma insulin, blood glucose and/or serum triglycerides.

In another aspect, the present invention relates to the use of a lipid compound according to any of the formulas (I)-(V) for the manufacture of a medicament for the prevention and/or treatment of: elevated triglyceride levels, LDL cholesterol levels, and/or VLDL cholesterol levels, a hyperlipidemic condition, e.g. hypertriglyceridemia (HTG), obesity or an overweight condition, body weight gain, a fatty acid liver disease, especially a non-alcoholic fatty liver disease (NAFLD), insulin resistance, hyperlipidemia, peripheral insulin resistance and/or a diabetic condition, especially type 2 diabetes.

The present invention also relates to lipid compounds according to any of the formulas (I)-(V) for the treatment and/or prevention of the conditions listed above.

Furthermore, the invention relates to methods for the treatment and/or prevention of the conditions listed above, comprising administering to a mammal in need thereof a pharmaceutically active amount of a lipid compound according to any of the formulas (I)-(V).

Furthermore, the lipid compounds according to any of the formulas (I)-(V) may be used in combating a disease selected from atherosclerosis, inflammations and cancer and chronic inflammatory diseases like psoriasis, rheumatoid arthritis etc. and brain disorders (MS, Alzheimer).

In addition to pharmaceutical uses, the lipid compounds according to any of the formulas (I)-(V) may be used as dietary supplements. Therefore in a further aspect, the present invention provides a food, food additive, food supplement or neutraceutical preparation comprising a lipid compound according to any of the formulas (I)-(V).

Cosmetic formulations or products comprising lipid compounds of any of the formulas (I)-(V) form a further aspect of the invention.

In a still further aspect the present invention provides radiolabelled analogues of compounds according to formula (1). Such radiolabelled analogues are particularly useful for use in diagnostic methods e.g. PET imaging.

Many of the intermediates formed during the preparation of the lipid compounds of the invention are themselves novel and useful compounds and these form a further aspect of the invention. Specific examples of such intermediates may be found in the reaction schemes below.

The present invention will now be further described by the following non-limiting examples.

EXAMPLE 1

General Synthesis

The lipid compounds of the general formula (I) can be prepared by combinations of carbonyl olefination reactions like the Wittig type of reactions, the Peterson reaction or the Julia reaction. More specifically: The lipid compounds of the general formula (I) where $R_1$ and $R_2$ is hydrogen and X is a carboxylate are prepared through the following processes.

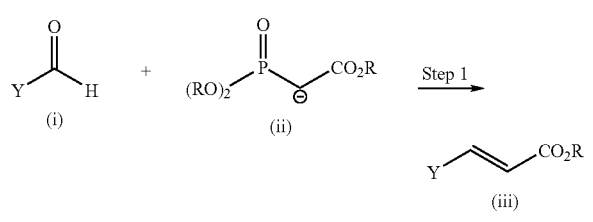

Reaction of an aldehyde (i) with a phosphoryl-stabilized carbanion [(RO)$_2$P(O)C$^-$HCO$_2$R] (ii) gives the mainly the (E)-α,β-unsaturated ester (iii) as the major product. The phosphoryl-stabilized carbanion can be generated by treatment of triethyl phosphonoacetate or trimethyl phosphonoacetate with a base, for example, alkali metal hydride such as sodium hydride, metal alkoxide such as sodium methoxide, organometallic compound such as butyl lithium, metal amide such as lithium diisopropyl amide, or other bases in a solvent such as DME (dimethoxyethane), tetrahydrofuran, benzene, toluene. The reaction can be performed at a reaction temperature of −78° C. to room temperature. The ester (iii) may be hydrolysed in a solvent such as ethanol or methanol to the carboxylic acid form by addition of a base such as lithium/sodium/potassium hydroxide in water at temperatures between 10-90° C. This may then, if desired, be esterified or amidated. The ester (iii) may be reduced to the alcohol or aldehyde.

The lipid compounds of the general formula (I) where $R_1$ is an alkyl group, fluorine or alkoxy group, $R_2$ is hydrogen and X is a carboxylate are prepared through the following processes.

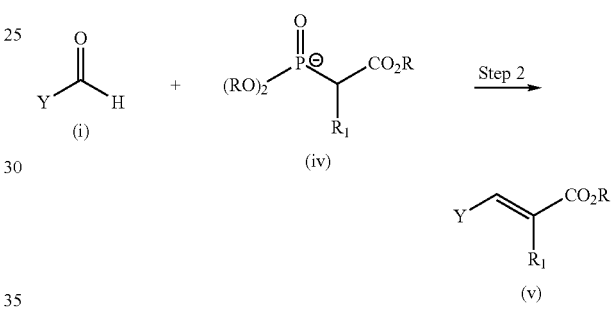

The process is analogous to Step 1 with the exception that the phosphonate is substituted in the 2-position with an alkyl group, a fluorine or alkoxy group.

The lipid compounds of the general formula (I) where $R_2$ is an alkyl group and $R_1$ is hydrogen and X is a carboxylate can be prepared through the following processes.

Method 1, Horner-Wadsworth-Emmons Reaction:

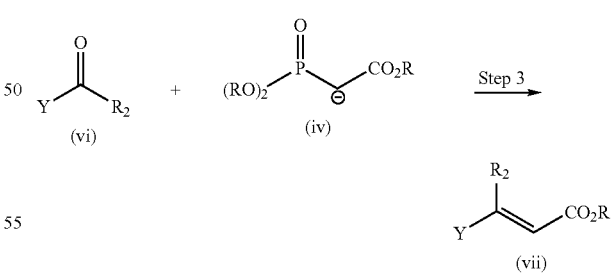

Method 2, Peterson Reaction:

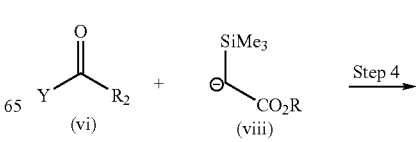

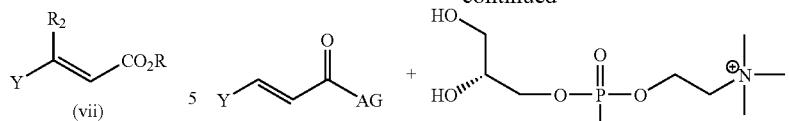

Step 3 is analogous to step 1 and 2, with the exception that the reaction temperature has to be raised to 0 to 80° C.

In Step 4, the enolate of α-trimethylsilyl acetate is utilized for the synthesis of the α,β-unsaturated ester (vii) from ketone (vi).

The lipid compounds of the general formula (I) where $R_2$ is an alkyl group and $R_1$ is hydrogen and X is a carboxylate can also be prepared through the following processes.

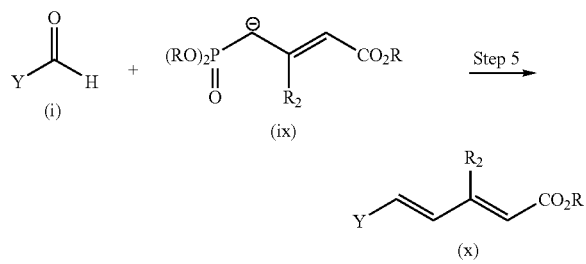

The unsaturated aldehydes, Y—C(O)H, may be prepared directly from the carboxylic esters of the naturally occurring unsaturated fatty acids; alpha-linolenic acid, oleic acid, conjugated linoleic acid, linoleic acid, eicosapentaenoic acid, etc. by reduction with diisobutylaluminiumhydride at −78° C. or by a two step procedure including reduction to an alcohol and then oxidation to an aldehyde. The aldehydes can also be prepared by degradation of the polyunsaturated fatty acids EPA and DHA as described by Holmeide et al. (*J. Chem. Soc., Perkin Trans.* 1, 2000, 2271). In this case one can start with purified EPA or DHA, but it is also possible to start with fish oil containing EPA and DHA in mixture. The reason for this is that DHA reacts faster in an iodolactonisation reaction than EPA to form an iodo δ-lactone (Corey et al, *Proc. Natl. Acad. Sci. USA*, 1983, 3581, Wright et al, *J. Org. Chem.*, 1987, 4399), Kuklev et al, *Phytochemistry*, 1992, 2401). Aldehydes can also be prepared from the α,β-unsaturated esters covered by the invention by reduction with diisobutylaluminiumhydride at −78° C. or by a two step procedure including reduction to an alcohol and then oxidation to an aldehyde.

The ketones can be prepared from naturally occurring unsaturated acids by reaction with two equivalents of an alkyllithium at −78° C. in a solvent like diethylether. They can also be prepared from aldehydes, like the ones already described, by reaction with an anion of a β-keto phosphonate like diethyl(2-oxo-propyl)phosphonate.

The lipid compounds of the general formula (I) wherein X is a carboxylic acid and in the form of a phospholipid can be prepared through the following processes.

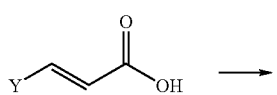

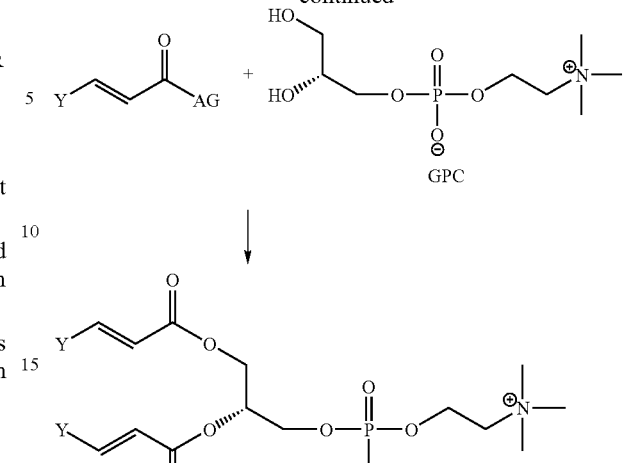

Acylation of sn-glycero-3-phosphocholine (GPC) with an activated fatty acid, such as fatty acid imidazolides, is a standard procedure in phosphatidylcholine synthesis. It is usually carried out in the presence of DMSO anion with DMSO as solvent (Hermetter; *Chemistry and Physics of lipids,* 1981, 28, 111). Sn-Glycero-3-phosphocholine, as cadmium (II) adduct can also be reacted with the imidazolide activated fatty acid in the presence of DBU (1,8-diazabicyclo[5.4.0]undec-7-ene] to prepare the phosphatidylcholine of the respective fatty acid (International application number PCT/GB2003/002582). Enzymatic transphosphatidylation can effect the transformation of phosphstidylcholine to phosphatidyletanolamine (Wang et al, *J. Am. Chem. Soc.,* 1993, 115, 10487).

Polyunsaturated fatty acids containing phospholipids may be prepared by various ways, mainly by chemical synthesis of phospholipids as described, by enzymatic esterification and transesterification of phospholipids or enzymatic transphosphatidylation of phospholipids. (Hosokawa, *J. Am. Oil Chem. Soc.* 1995, 1287, Lilja-Hallberg, Biocatalysis, 1994, 195). For such enzymatic applications a preferred embodiment of the invention is a lipid compound according to the general formula I wherein $R_1$ and $R_2$ are hydrogen.

The lipid compounds of the general formula (I) wherein X is a carboxylic acid and in the form of a triglyceride can be prepared through the following processes. Excess of the novel fatty acid can be coupled to glycerol using dimethylaminopyridine (DMAP) and 2-(1H-benzotriazol-1-yl)-N,N,N',N'-tetramethyluroniumhexafluorophosphate (HBTU).

The lipid compounds of the general formula (I) wherein X is a carboxylic acid and in the form of a diglyceride can be prepared by reaction of the fatty acid (2 equivalents) with glycerol (1 equivalent) in the presence of 1,3-dicyclohexylcarbondiimide (DCC) and 4-dimethylaminopyridine (DMAP).

The lipid compounds of the general formula (I) wherein X is a carboxylic acid and in the form of a monoglyceride can be prepared through the following processes.

Acylation of 1,2-O-isopropylidene-sn-glycerol with a fatty acid using DCC and DMAP in chloroform gives a monodienoylglycerol. Deprotection of the isopropylidene group can be done by treating the protected glycerol with an acidic (HCl, acetic acid etc.) (O'Brian, *J. Org. Chem.,* 1996, 5914).

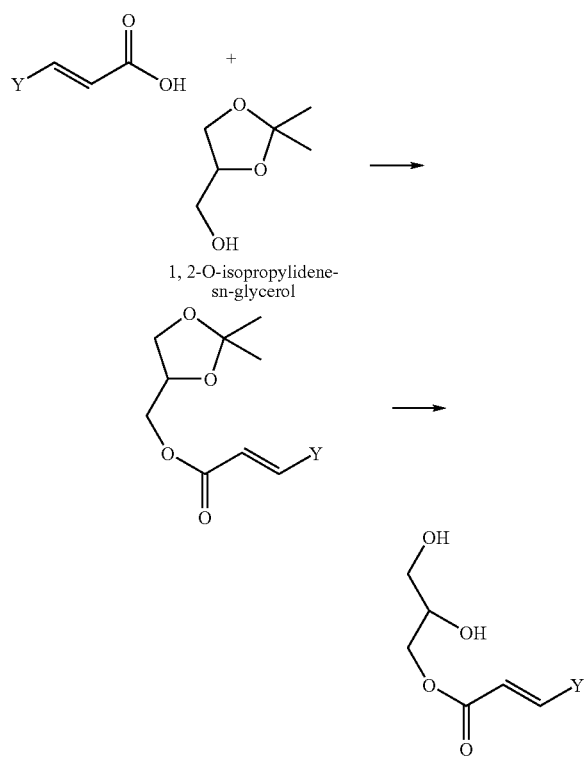

1,2-O-isopropylidene-sn-glycerol

There are several common synthetic methods for the preparation of monoglycerides with the fatty acid in 2-position. One method utilizes esterification of the fatty acid with glycidol in the presence of 1-(3-dimethylaminopropyl)-3-ethyl-carbodiimidehydrochloride (EDC) and 4-dimethylaminopyridine (DMAP) to produce a glycidyl derivative. Treatment of the glycidyl derivative with trifluoroacetic anhydride (TFAA) prior to trans-esterification the monoglyceride is obtained (Parkkari et al, *Bioorg. Med. Chem. Lett.* 2006, 2437).

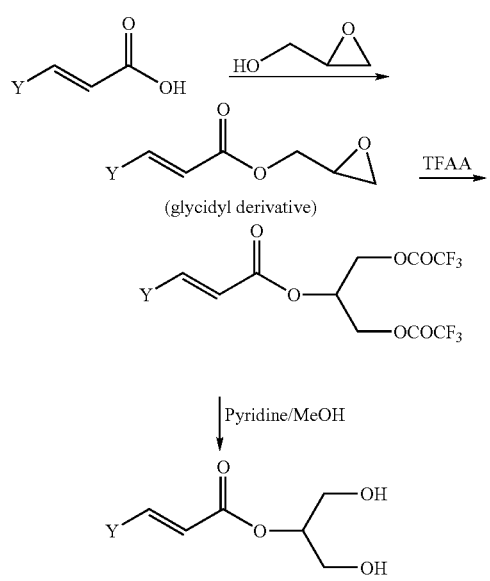

Further common methods for the preparation of mono-, di- and tri-glycerides of fatty acid derivatives are described in international patent application, PCT/FR02/02831.

It is also possible to use enzymatic processes (lipase reactions) for the transformation of a fatty acid to a mono-, di-, tri-glyceride. A 1,3-regiospecific lipase from the fungus *Mucor miehei* can be used to produce triglycerides or diglycerides from polyunsaturated fatty acids and glycerol. A different lipase, the non-regiospecific yeast lipase from *Candida antartica* is highly efficient in generating triglycerides from polyunsaturated fatty acids (Haraldsson, *Pharmazie*, 2000, 3). For this enzymatic application a preferred embodiment of the invention is a lipid compound according to the general formula I wherein $R_1$ and $R_2$ are hydrogen.

Synthesis/Preparation of Lipid Compounds According to the Invention

The invention will now be described in more detail by the following examples, which are not to be constructed as limiting the invention.

Moreover, in the following examples the structures were verified by NMR. The NMR spectra were recorded in $CDCl_3$ with a Bruker Avance DPX 200 or with a Bruker Avance DPX 300 instrument. J values are given in Hz. Mass spectra were recorded with a LC/MS Agilent 1100 series, with a G 1956 A mass spectrometer (electrospray, 3000 V). All reactions run under inert atmosphere were performed under nitrogen atmosphere.

| Abbreviations | |
|---|---|
| THF | tetrahydrofuran |
| EtOAc | ethylacetate |
| DBU | 1,8-diazabicyclo[5.4.0]undec-7-ene |
| LAH | lithium aluminium hydride |
| BuLi | butyl lithium |
| NaH | sodium hydride |
| t | triplet |
| s | singlet |
| d | doublet |
| q | quartet |
| m | multiplet |
| bs | broad singlet |

EXAMPLE 1

Ethyl (2E,7Z,10Z,13Z,16Z,19Z)-2-methyl-docosa-2,7,10,13,16,19-hexaenoate (1)

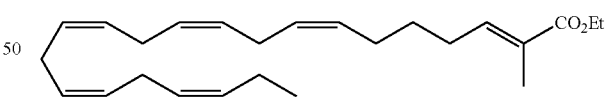

Triethyl 2-phosphonopropionate (414 µl, 1.9 mmol) was added to a suspension of sodium hydride (81 mg, 60% dispersion in mineral oil, 2.0 mmol) in dry THF (5 ml) at 0° C. After 30 minutes at room temperature the mixture was cooled to 0° C. and (all-Z)-Icosa-5,8,11,14,17-pentaenal (500 mg, 1.7 mmol) in THF (1 ml) was added. The mixture was stirred for 40 minutes at 0° C. A saturated aqueous $NH_4Cl$ solution of was added and the phases were separated. The aqueous phase was extracted with a mixture of hexane:EtOAc (8:2). The combined organic phases were washed with brine, water and dried ($MgSO_4$). Evaporation of the solvents under reduced pressure followed by flash chromatography on silica gel (9:1 hexane-EtOAc) gave the ester 1 (550 mg, 85%), (2E:2Z=7:1 (GC)).

$\delta_H$(300 MHz): 0.95 (t, J 7.5, 3H, CH$_3$), 1.25 (t, J 7.1, 3H), 1.51 (m, 2H), 1.84 (d, J 1, CH$_3$, 3H), 1.9-2.2 (m, 6H), 2.7-2.9 (m, 8H), 4.20 (q, J 7.1, 2H), 5.2-5.5 (m, 10H), 6.88 (td, J 7.5, J 1, 1H).

EXAMPLE 2

(2E,7Z,10Z,13Z,16Z,19Z)-2-methyl-docosa-2,7,10,13,16,19-hexaenoic acid (2)

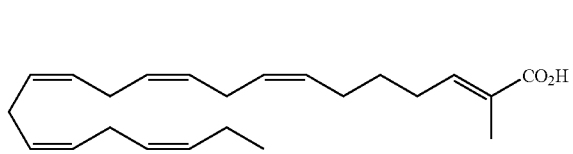

Ethyl (2E,7Z,10Z,13Z,16Z,19Z)-2-methyl-docosa-2,7,10,13,16,19,hexaenoate (1) was hydrolysed, and the stereoisomers were separated by flash chromatography on silica gel (8:2 hexane-EtOAc).

Compound 2: E-isomer; $\delta_H$(300 MHz): 0.96 (t, J 7.5, 3H, CH$_3$), 1.53 (m, 2H), 1.82 (d, J 1, CH$_3$, 3H), 1.9-2.2 (m, 6H), 2.7-2.9 (m, 8H), 5.2-5.5 (m, 10H), 6.91 (td, J 7.5, J 1, 1H); $\delta_c$(75 MHz) 11.93, 14.23, 20.51, 25.50, 25.60, 26.82, 28.29, 28.39, 126.97, 127.26, 127.83, 128.04, 128.06, 128.20, 128.27, 128.51, 129.29, 131.97, 144.87, 173.80.

Compound 28: Z-isomer: $\delta_H$(300 MHz): 0.95 (t, J 7.5, 3H, CH$_3$), 1.48 (m, 2H), 1.90 (br d, J 1.4, 3H, CH$_3$), 2.1-2.3 (m, 4H), 2.53 (m, 2H), 2.7-2.9 (m, 8H), 5.2-5.5 (m, 10H), 6.08 (td, J 7.4, J 1.4, 1H); $\delta_c$(75 MHz) 14.25, 20.48, 20.54, 25.53, 25.62, 26.92, 29.35, 29.45, 126.83, 127.02, 127.89, 128.01, 128.14, 128.17, 128.20, 128.38, 128.54, 129.69, 132.02, 146.45, 173.21.

EXAMPLE 3

Preparation of ethyl (2E,7Z,10Z,13Z,16Z,19Z)-3-methyl-docosa-2,7,10,13,16,19-hexaenoate (3)

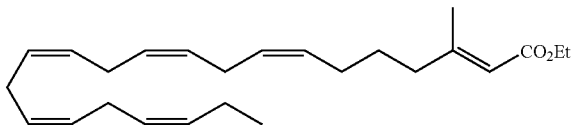

Triethylphosphonoacetate (288 μl, 1.4 mmol) was added to a suspension of sodium hydride (58 mg, 60% dispersion in mineral oil, 1.4 mmol) in dry benzene (8 ml) at room temperature. After 30 minutes a solution of (all-Z)-henicosa-6,9,12,15,18-pentaen-2-on (400 mg, 1.3 mmol) in benzene (4 ml) was added. The mixture was stirred for 48 hrs. at RT. Water was added and the mixture extracted with hexane. The extract was washed with water and dried (MgSO$_4$). Evaporation of the solvents under reduced pressure followed by flash chromatography on silica gel (95:5 hexane-EtOAc) gave the ester 3 (270 mg, 53%) as an oil. $^1$H-NMR (200 MHz, CDCl$_3$): δ 0.94 (t, 3H), 1.23 (t, 3H), 1.49-1.57 (m, 2H), 1.99-2.12 (m, 6H), 2.12 (s, 3H), 2.76-2.83 (m, 8H), 4.10 (q, 2H), 5.30-5.37 (m, 10H), 5.63 (s, 1H); $^{13}$C-NMR (50 MHz, CDCl$_3$): δ 14.18, 14.25, 18.61, 20.48, 25.46, 25.56, 25.59, 26.63, 27.26, 28.06, 40.33, 59.33, 126.93, 127.78, 128.00 (2 signals), 128.16, 128.17, 128.42, 128.47 (2 signals), 129.29, 131.92, 159.64, 166.68.

EXAMPLE 4

Preparation of (2E,7Z,10Z,13Z,16Z,19Z)-3-methyl-docosa-2,7,10,13,16,19-hexaenoic acid (4)

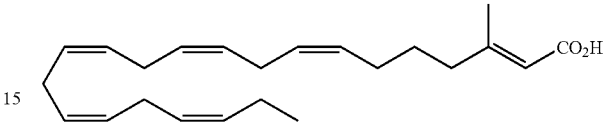

Ethyl (2E,7Z,10Z,13Z,16Z,19Z)-3-methyl-docosa-2,7,10,13,16,19-hexaenoate (3) was dissolved in methanol (9 ml) and added LiOH (220 mg, 4.89 mmol) in water (3 ml) and the mixture was heated at 50° C. for 2 hrs. The mixture was cooled, and diluted hydrochloric acid was added to pH 2. Extraction with diethylether, drying (MgSO$_4$) and evaporation of solvents under reduced pressure afforded the acid 4. The acid was purified by flash chromatography on silica gel (8:2 hexane-EtOAc); $\delta_H$(300 MHz) 0.95 (t, J 7.5, 3H, CH$_3$), 1.55 (m, 2H), 2.0-2.2 (m, 6H), 2.15 (d, J 1.3, 3H, CH$_3$), 2.7-2.9 (m, 8H), 5.2-5.5 (m, 10H), 5.68 (br s, 1H); $\delta_c$(75 MHz) 14.24, 19.04, 20.53, 25.51, 25.60, 25.62, 25.64, 26.67, 27.28, 40.67, 115.24, 126.99, 127.84, 128.05, 128.11, 128.19, 128.22, 128.53, 128.57, 129.23, 132.00, 163.05, 172.31.

EXAMPLE 5

(2E,7Z,10Z,13Z,16Z,19Z)-3-methyl-docosa-2,7,10,13,16,19-hexaen-1-ol (5)

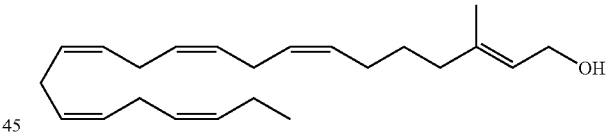

Ethyl (2E,7Z,10Z,13Z,16Z,19Z)-3-methyl-docosa-2,7,10,13,16,19-hexaenoate (2E:2Z=9:1), (0.40 g, 1.08 mmol) was dissolved in dry THF (5 mL) and added dropwise to a cold suspension of LAH (0.045 g, 1.19 mmol) in dry THF (10 mL). The mixture was stirred at 0° C. under inert atmosphere for 30 minutes, followed by 18 hours at ambient temperature. The reaction was quenched by addition of 10% NH$_4$Cl (20 mL) and the mixture was extracted twice with heptane (30 mL). The combined organic extracts were washed with brine (20 mL) and dried (Na$_2$SO$_4$). Purification by flash chromatography (heptane:EtOAc 4:1) afforded 0.16 g (45%) of 3-methyl-(2E,7Z,10Z,13Z,16Z,19Z)-docosa-2,7,10,13,16,19-hexaen-1-ol as a colourless oil.

Compound 3, E-isomer: $^1$H-NMR (200 MHz, CDCl$_3$): δ 0.95 (t, 3H), 1.32-1.50 (m, 2H), 1.64 (s, 3H), 1.97-2.09 (m, 6H), 2.76-2.85 (m, 8H), 4.11 (d, J 6.8, 2H), 5.27-5.42 (m, 11H); $^{13}$C-NMR (50 MHz, CDCl$_3$): δ 14.21, 16.12, 20.50, 25.48 (2 signals), 25.58 (3 signals), 26.79, 27.59, 39.04, 59.28, 123.42, 126.96, 127.83, 127.94, 127.98, 128.08, 128.16, 128.37, 128.50, 130.23, 131.98; MS (electrospray): 351.2 [M+Na]$^+$.

Compound 29, Z-isomer:

Further elution afforded 0.01 g (28%) of (all-Z)-3-methyl-docosa-2,7,10,13,16,19-hexaen-1-ol (29) as a colourless oil. $^1$H-NMR (200 MHz, CDCl$_3$): δ 0.95 (t, 31H), 1.30-1.50 (m, 2H), 1.71 (s, 3H), 2.02-2.09 (m, 6H), 2.76-2.85 (m, 8H), 4.09 (d, J 7.1, 2H), 5.28 (s, 1H), 5.31-5.41 (m, 101H); MS (electrospray): 351.2 [M+Na]$^+$.

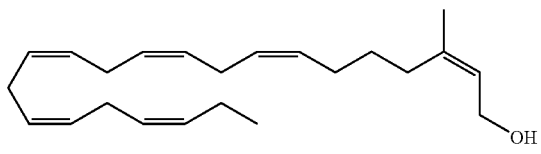

EXAMPLE 6

Ethyl (2E,11Z,14Z,17Z)-2-methyl-eicosa-2,11,14,17-tetraenoate (6)

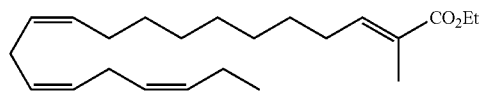

Triethylphosphonopropionate (386 μl, 1.8 mmol) was added to a suspension of sodium hydride (72 mg, 60% dispersion in mineral oil, 1.8 mmol) in dry THF (5 ml) at 0° C. After 30 minutes a solution of (all-Z)-octadeca-9,12,15-trienal (300 mg, 1.15 mmol) in THF (2 ml) was added. The mixture was stirred for 1 hrs. at 0° C. An aqueous solution of NH$_4$Cl was added and the mixture extracted with EtOAc. The extract was washed with water and dried (MgSO$_4$). Evaporation of the solvents under reduced pressure followed by flash chromatography on silica gel (95:5 hexane-EtOAc) gave the ester 6 (180 mg, 45%). δ$_H$(300 MHz) 0.95 (t, J 7.5, 3H, CH$_3$), 1.2-1.5 (m, 13H), 1.80 (s, CH$_3$, 3H), 2.0-2.2 (m), 2.78 (t, J 5.8, 4H), 4.16 (q, J 7.1, 2H, CH$_2$), 5.2-5.4 (m, 6H), 6.73 (dt, J 7.5, J 1.3, 1H); δ$_c$(75 MHz) 12.31, 14, 25, 20, 53, 25, 51, 25.60, 27.20, 28, 56, 28.66, 29.178, 29.34, 29.60, 60.33, 127.10, 127.70, 128.26, 130.27, 131.94, 142.37, 168.30.

EXAMPLE 7

(2E,11Z,14Z,17Z)-2-methyl-eicosa-2,11,14,17-tetraenoic acid (7)

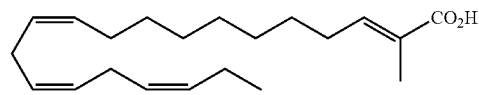

Ethyl (2E,11Z,14Z,17Z)-2-methyl-eicosa-2,11,14,17-tetraenoate (6) (160 mg, 0.46 mmol) was dissolved in methanol (3 ml) and added LiOH (193 mg, 4.6 mmol) in water (3 ml) and the mixture was heated at 50° C. for 2 hrs. The mixture was cooled, and diluted hydrochloric acid was added to pH 2. Extraction with diethylether, drying (MgSO$_4$) and evaporation of solvents under reduced pressure afforded the acid 7. The acid was purified by flash chromatography on silica gel (8:2 hexane-EtOAc); δ$_H$(300 MHz) 0.95 (t, J 7.5, 3H, CH$_3$), 1.2-1.5 (m, 10H), 1.81 (s, 3H, CH$_3$), 2.0-2.2 (m, 6H), 2.79 (t, J 5.8, 4H), 5.2-5.4 (m, 6H), 6.90 (dt, J 7.5, J 1.3, 1H); δ$_c$(75 MHz) 11.93, 14.25, 20.53, 25.51, 25.60, 27.19, 28.40, 28.87, 29.16, 29.31, 29.58, 126.94, 127.10, 127.71, 128.24, 128.25, 130.25, 131.93, 145.41, 173.76.

EXAMPLE 8

Ethyl (2Z/E,11Z,14Z,17Z)-2-ethyl-eicosa-2,11,14,17-tetraenoate (30)

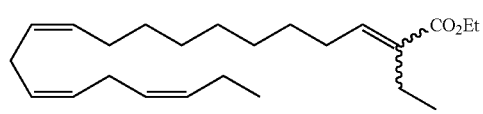

NaH (60% in mineral oil, 0.080 g, 2.00 mmol) was suspended in dry THF (10 mL) under inert atmosphere. The suspension was cooled to 0° C., dropwise added triethyl 2-phosphonobutyrate (0.47 mL, 2.00 mmol) and stirred at 0° C. for 20 minutes. To this mixture was added a solution of (all Z)-octadeca-9,12,15-trienal (PRB-73, 0.35 g, 1.33 mmol) in dry THF (5 mL) and the resulting mixture was stirred at ambient temperature for 30 minutes. The mixture was diluted with diethyl ether (25 mL), washed with water (20 mL) and dried (Na$_2$SO$_4$). Purification by flash chromatography (heptane:EtOAc 98:2) afforded 0.47 g (99%) of the title compound 30 (2E:2Z=1:1 mixture).

$^1$H-NMR (200 MHz, CDCl$_3$):

E-isomer: δ 0.91-1.04 (m, 6H), 1.23-1.41 (m, 13H), 2.01-2.26 (m, 8H), 2.76-2.81 (m, 4H), 4.17 (q, 2H), 5.28-5.41 (m, 6H), 6.86 (t, J 7.53, 1H).

Z-isomer: δ 0.91-1.04 (m, 6H), 1.23-1.41 (m, 13H), 2.01-2.26 (m, 8H), 2.76-2.81 (m, 4H), 4.17 (q, 2H), 5.28-5.41 (m, 6H), 5.80 (t, J 7.39, 1H).

$^{13}$C-NMR (50 MHz, CDCl$_3$):

Z- and E-isomer: δ 13.65, 13.94, 14.26 (two signals), 20.01, 20.54, 25.51, 25.60, 27.23 (two signals), 27.54, 28.33, 28.87, 29.18, 29.23, 29.30, 29.38, 29.51, 29.63, 59.63, 60.22, 127.10, 127.65, 127.70, 128.25 (two signals), 130.27, 130.33, 131.93, 133.63, 133.93, 140.30, 142.01, 168.35 (two signals).

MS (electrospray): 383.8 [M+Na]$^+$.

EXAMPLE 9

(2E,11Z,14Z,17Z)-2-ethyl-eicosa-2,11,14,17-tetraen-1-ol (9)

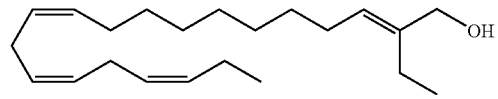

A suspension of LAH (0.027 g, 0.70 mmol) in dry THF (7 mL) was cooled to 0° C. under inert atmosphere and dropwise added a solution of ethyl (2E/Z,11Z,14Z,17Z) 2-ethyl-eicosa-2,11,14,17-tetraenoate (30) (2E:2Z=1:1), (0.23 g, 0.68 mmol). The mixture was stirred at 0° C. for 30 minutes and then at ambient temperature for 30 minutes. Saturated NH$_4$Cl (15 mL) was added and the mixture was extracted twice with heptane (20 mL). The combined organic extracts were washed with brine (20 mL) and dried (Na$_2$SO$_4$). Purification by flash chromatography (heptane:EtOAc 8:1) afforded 0.050 g (23%) of (2E,11Z,14Z,17Z) 2-ethyl-eicosa- 2,11,14,17-tetraen-1-ol (9) as a colourless oil. $^1$H-NMR (200 MHz, CDCl$_3$): δ 0.82-1.04 (2×t, 6H), 1.20-1.40 (m, 10H), 1.99-2.17 (m, 8H), 2.78 (m, 4H), 4.12 (s, 2H), 5.24-5.44 (m, 7H); $^{13}$C-NMR (50 MHz, CDCl$_3$): δ 12.87, 14.24, 20.52, 25.49, 25.58, 27.19, 27.48, 27.78, 29.22 (2 signals), 29.39, 29.61, 30.08, 60.30, 127.09, 127.59, 127.64, 128.23 (2 signals) 130.29, 131.91, 139.84; MS (electrospray): 341.3 [M+Na]$^+$.

Further elution (heptane:EtOAc 6:1) afforded 0.020 g (18%) of (all-Z) 2-ethyl-eicosa-2,11,14,17-tetraen-1-ol (31) as a pale yellow oil. $^1$H-NMR (200 MHz, CDCl$_3$): δ 0.82-0.99 (2×t, 6H), 1.15-1.40 (m, 10H), 1.95-2.15 (m, 8H), 2.79 (m, 4H), 4.02 (s, 2H), 5.23-5.44 (m, 7H); $^{13}$C-NMR (50 MHz, CDCl$_3$); MS (electrospray): 341.3 [M+Na]$^+$.

EXAMPLE 10

Ethyl (2E,5Z,8Z,11Z,14Z,17Z)-2-methyl-icosa-2,5,8,11,14,17-hexaenoate (8)

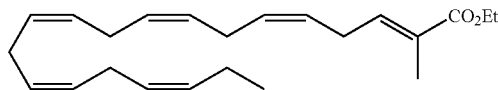

Triethyl 2-phosphonopropionate (366 μl, 1.7 mmol) was added to a suspension of sodium hydride (70 mg, 60% dispersion in mineral oil, 1.75 mmol) in dry THF (5 ml) at 0° C. After 50 minutes at 0° C. the mixture was cooled to −25° C. and (all-Z)-octadeca-3,6,9,12,15-pentaenal (400 mg, 1.55 mmol) in THF (1 ml) was added. The mixture was stirred for 50 minutes at −25° C. A saturated aqueous NH$_4$Cl solution of was added and the phases were separated. The aqueous phase was extracted with hexane. The combined organic phases were washed with brine, water and dried (MgSO$_4$). Evaporation of the solvents under reduced pressure followed by flash chromatography on silica gel (95:5 hexane-EtOAc) gave the ester 8. δ$_H$(300 MHz): 0.95 (t, J 7.5, 3H, CH$_3$), 1.26 (t, J 7.1, 3H), 1.84 (d, J 1.3, 3H, CH$_3$), 2.05 (m, 2H), 2.7-2.9 (m, 8H), 2.92 (t, J 6.9, 2H), 4.16 (q, J 7.1, 2H), 5.2-5.5 (m, 11H); δ$_c$(75 MHz) 12.36, 14.22, 20.52, 25.50, 25.59, 25.61, 25.68, 26.95, 60.42, 125.86, 126.95, 127.72, 127.78, 127.92, 128.09, 128.30, 128.41, 128.56, 129.48, 131.99, 139.69, 168.03;

EXAMPLE 11

Ethyl (2E/Z,7Z,10Z,13Z,16Z,19Z)-ethoxy-docosa-2,7,10,13,16,19-hexaenoate (32)

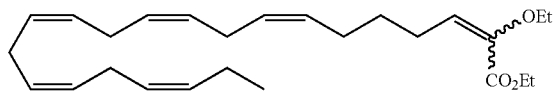

NaH (60% in mineral oil, 0.28 g, 7.07 mmol) was suspended in dry THF (10 mL) under inert atmosphere and given 0° C. A solution of triethyl-2-ethoxy-2-phosphonoacetate (3.79 g, 14.1 mmol) in dry THF (10 mL) was added dropwise and the resulting pale yellow solution was stirred at 0° C. for 20 minutes. Octadeca-2E,6Z,9Z,12Z,15Z-pentaenal (1.35 g, 4.71 mmol) in dry THF (10 mL) was then added, the mixture was stirred at ambient temperature for 2.5 hours and diluted with diethyl ether (100 mL). The organic layer was washed with water (50 mL) and dried (Na$_2$SO$_4$). Purification by flash chromatography (heptane:EtOAc 98:2) afforded 1.36 g (72%) of the title compound 32 as a 1:1 mixture of the 2E- and 2Z-isomer as colourless oils. $^1$H-NMR (200 MHz, CDCl$_3$): □ 0.95 (t, 3H), 1.23-1.34 (m, 6H), 1.35-1.52 (m, 2H), 1.95-2.10 (m, 4H), 2.20-2.50 (2×m, 2H), 2.70-2.90 (m, 8H), 3.60-3.90 (2×q, 2H), 4.10-4.30 (2×q, 2H) 5.21-5.45 (m, 10.5H), 6.23 (t, 0.5H); MS (electrospray): 423.3 [M+Na]$^+$.

EXAMPLE 12

Ethyl (2Z,7Z,10Z,13Z,16Z,19Z)-ethoxy-docosa-2,7,10,13,16,19-hexaenoate (33)

50 mg of the title compound as a 1:1 mixture of isomers was heated to 100° C. neat in the presents of a catalytic amount of thiophenol (one drop) under inert atmosphere for three hours. The mixture was cooled and purified by flash chromatography to afford 20 mg (40%) of pure ethyl (2Z,7Z,10Z,13Z,16Z,19Z) 2-ethoxy-docosa-2,7,10,13,16,19-hexaenoate as a pale yellow oil. $^1$H-NMR (200 MHz, CDCl$_3$): δ 0.95 (t, J 7.50, 3H), 1.23-1.34 (m, 6H), 1.40-1.54 (m, 2H), 1.95-2.10 (m, 4H), 2.22 (q, J 7.60, 2H), 2.70-2.90 (m, 8H), 3.82 (q, J 7.05, 2H), 4.15-4.26 (q, J 7.11, 2H) 5.21-5.45 (m, 1H), 6.23 (t, J 7.60, 1H); MS (electrospray): 423.3 [M+Na]$^+$.

EXAMPLE 13

2-ethoxy-docosa-2E,7Z,10Z,13Z,16Z,19Z-hexaenoic acid (26)

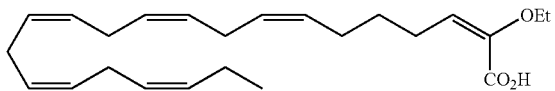

A mixture of ethyl (2E/Z,7Z,10Z,13Z,16Z,19Z)-2-ethoxy-docosa-2,7,10,13,16,19-hexaenoate (32) (E:Z=1:1, 0.40 g, 1.00 mmol) in ethanol (8 mL) under inert atmosphere was added a solution of LiOH×H$_2$O (0.33 g, 8.00 mmol) in water (3 mL). The resulting turbid mixture was given 70° C. for 30 minutes and then stirred at ambient temperature for 18 hours. 1M HCl was added until pH=1 and the mixture was extracted twice with heptane (15 mL). The combined organic extracts were dried (Na$_2$SO$_4$) and purified by flash chromatography (heptane:EtOAc 9:1 then 4:1). This afforded 0.18 g (48%) of the title compound 26 as colorless oil. (2E:2Z=1:3).

Z-isomer: δ 0.91-0.99 (t, J 7.5, 3H), 1.28 (t, J 7.0, 3H), 1.48 (quint, J 7.4, 2H), 1.98-2.09 (m, 4H), 2.24 (q, J 7.5, 2H), 2.70-2.90 (m, 8H), 3.85 (q, J 7.0, 2H), 5.25-5.40 (m, 10H), 6.42 (t, J 7.6, 1H), 10.74 (s, broad, 1H)

E-isomer: δ 0.86 (t, 3H), 1.34 (t, J 7.0, 3H), 1.42 (m, 2H), 1.98-2.09 (m, 4H), 2.54 (q, J 7.6, 2H), 2.70-2.90 (m, 8H), 3.75 (q, J 6.9, 2H), 5.20-5.40 (m, 11H), 10.74 (s, broad, 1H), (minor isomer);

E- and Z-isomer: $^{13}$C-NMR (75 MHz, CDCl$_3$): δ 14.23, 15.33, 20.53, 25.52 (2 signals), 25.61 (3 signals), 26.94, 28.45, 28.55, 30.05, 30.34, 68.30, 98.01, 126.99, 127.85, 128.05, 128.07 (2 signals), 128.18, 128.22, 128.25, 128.46, 128.53, 129.33, 131.72, 132.00, 174.90, (both isomers); MS (electrospray): 371.2 [M–H]⁻.

EXAMPLE 14

(2E,7Z,10Z,13Z,16Z,19Z)-2-ethoxy-docosa-2,7,10,13,16,19-hexaen-1-ol (27) and (all-Z) 2-ethoxy-docosa-2,7,10,13,16,19-hexaen-1-ol (34)

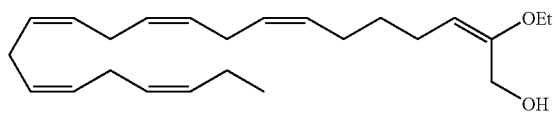

LAH (0.021 g, 0.55 mmol) was suspended in dry THF (8 mL) and held at 0° C. under inert atmosphere. To this suspension was dropwise added a solution of ethyl-(2E/Z,7Z,10Z,13Z,16Z,19Z)-2-ethoxy-docosa-2,7,10,13,16,19-hexaenoate (32) (1:1, 0.20 g, 0.50 mmol) in dry THF (2 mL). The resulting mixture was stirred at 0° C. for ten minutes, followed by 50 minutes at ambient temperature. Saturated NH₄Cl (15 mL) was added and the mixture was extracted twice with heptane (20 mL). The combined organic extracts were washed with brine (15 mL) and dried (Na₂SO₄). Purification by flash chromatography (heptane:EtOAc 9:1) afforded 0.033 g (18%) of 2-ethoxy-docosa-2E,7Z,10Z,13Z,16Z,19Z-hexaen-1-ol (27) as a colorless oil. $^1$H-NMR (200 MHz, CDCl₃): δ 0.95 (t, J=7.49 Hz, 3H), 1.28 (t, J=6.96 Hz, 3H), 1.30-1.44 (quint, J=7.62 HZ, 2H), 1.95-2.09 (m, 6H), 2.70-2.90 (m, 8H), 3.68 (q, J=6.97 Hz, 2H), 4.12 (d, J=5.31 Hz, 2H), 4.46 (t, J=7.58 Hz, 1H), 5.26-5.38 (m, 10H); $^{13}$C-NMR (50 MHz, CDCl₃): δ 14.24, 14.56, 20.53, 25.51, 25.60, 25.74, 26.62, 30.91, 59.43, 62.20, 99.42, 126.99, 127.86, 127.98, 128.05, 128.11, 128.20, 128.39, 128.54, 129.85, 132.01, 153.48 (2 signals hidden); MS (electrospray): 381.3 [M+Na]⁺.

0.11 g (61%) of (all-Z) 2-ethoxy-docosa-2,7,10,13,16,19-hexaen-1-ol (34) was also isolated as a colourless oil. $^1$H-NMR (200 MHz, CDCl₃): δ 0.94 (t, J=7.51 Hz, 3H), 1.25 (t, J=7.02 Hz, 3H), 1.30-1.50 (quint, J=7.82 Hz, 2H), 1.98-2.15 (m, 6H), 2.70-2.85 (m, 8H), 3.84 (q, J=7.02 Hz, 2H), 4.05 (s, broad, 1H), 4.78 (t, J=7.21 Hz, 1H), 5.20-5.45 (m, 10H); $^{13}$C-NMR (50 MHz, CDCl₃): δ 14.24, 15.53, 20.52, 24.45, 25.51, 25.60, 26.94, 29.61, 62.45, 64.77, 112.63, 126.99, 127.86, 127.92, 128.12, 128.18, 128.45, 128.53, 129.99, 131.99, 152.87 (3 signals hidden); MS (electrospray): 381.3 [M+Na]⁺.

EXAMPLE 15

Ethyl (2E,4E,8Z,11Z,14Z,17Z)-icosa-2,4,6,11,14,17-hexaenoate (12)

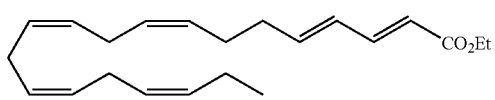

Potassium carbonate (395 mg, 2.9 mmol) in water (286 μl) was added to a vigorously stirred mixture of (2E,6Z,9Z,12Z,15Z)-octadeca-2,6,9,12,15-pentaenal (370 mg, 1.4 mmol) and triethylphosphonoacetate (344 ml, 1.72 mmol) at room temperature. The mixture was stirred for 48 h at room temperature, water was added, and the phases were separated. The aqueous phase was extracted with hexane. The combined organic phases were washed with water and dried (MgSO₄). Evaporation of the solvents under reduced pressure followed by flash chromatography on silica:gel (95:5 hexane-EtOAc) gave the ester (180 mg, 39%) and recovered aldehyde (80 mg), δ$_H$(300 MHz): 0.95 (t, J 7.5, 3H, CH₃), 1.26 (t, J 7.1, 3H), 2.04 (m, 2H), 2.1-2.3 (m, 4H), 2.7-2.9 (m, 6H), 4.17 (q, J 7.1, 2H), 5.2-5.5 (m, 8H), 5.77 (d, J 15.4, 1H), 6.1-6.2 (m, 2H), 7.22 (dd, J 15.4, J 9.9, 1H); δ$_c$(75 MHz) 14.23, 14.28, 20.53, 25.51, 25.60, 25.65, 26.41, 32.88, 60.14, 119.56, 126.97, 127.81, 128.02, 128.20, 128.53, 128.64, 128.75, 132.00, 143.45, 144.77, 167.18.

EXAMPLE 16

(2E,4E,8Z,11Z,14Z,17Z)-icosa-2,4,8,11,14,17-hexaenoic acid (13)

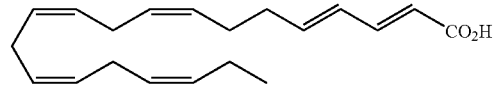

Ethyl (2E,4E,8Z,11Z,14Z,17Z)-icosa-2,4,6,11,14,17-hexaenoate (340 mg, 1.04 mmol) was dissolved in isopropanol (13 ml) and added LiOH (87 mg, 2.1 mmol) in water (5 ml) and the mixture was stirred at room temperature over night. The reaction mixture was poured into water and pH adjusted to pH 2-3 with HCl. The solution was extracted with ethyl acetate/hexane, drying (MgSO₄) and evaporation of solvents under reduced pressure afforded the acid 13. The acid was purified by flash chromatography on silica gel (8:2 hexane-EtOAc); 0.96 (t, J 7.5, 3H, CH₃), 2.04 (m, 2H), 2.1-2.3 (m, 4H), 2.7-2.9 (m, 6H), 5.2-5.5 (m, 8H), 5.77 (d, J 15.3, 1H), 6.1-6.2 (m, 2H), 7.31 (dd, J 15.4, J 10.1, 1H); δ$_c$(75 MHz) 14.25, 20.55, 25.54, 25.63, 25.67, 26.33, 32.96, 118.49, 126.99, 127.82, 128.00, 128.26, 128.58, 128.64, 128.88, 132.05, 145.05, 147.26, 172.08

EXAMPLE 17

Ethyl (2E,4E,7Z,10Z,13Z-16Z-19Z)-docosa-2,4,7,13,16,19-heptaenoate (14)

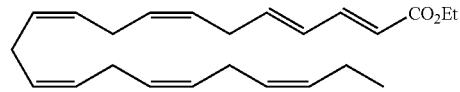

Step 1:

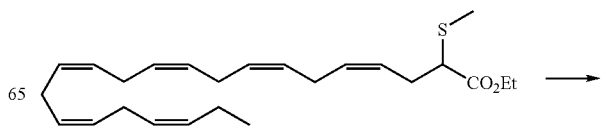

-continued

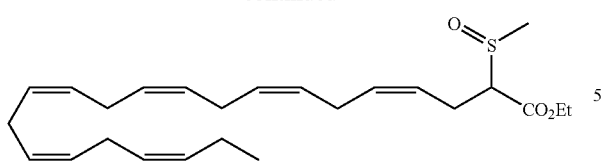

Ethyl (all-Z)-2-methanesulfanyl-docosa-4,7,10,13,16,19-hexaenoate (2.00 g, 4.97 mmol) was dissolved in CH$_2$Cl$_2$ (50 mL) and cooled to −20° C. under inert atmosphere. A solution of 3-chloroperbenzoic acid (mCPBA, 1.01 g, 4.97 mol) in CH$_2$Cl$_2$ (20 mL) was added dropwise this mixture over five minutes and the resulting mixture was stirred at −20° C. for one hour. The cold mixture was portioned between saturated Na$_2$SO$_3$ (100 mL) and diethyl ether (100 mL). The organic layer was washed twice with saturated NaHCO$_3$ (100 mL) and dried (Na$_2$SO$_4$).

Purification by flash chromatography (heptane:EtOAC 4:1 then 1:1 then heptane:EtOAc) afforded 0.73 g (35%) of ethyl (all-Z)-2-methanesulfinyl-docosa-4,7,10,13,16,19-hexaenoate as a colourless oil. $^1$H-NMR (200 MHz, CDCl$_3$): δ 0.95 (t, 3H), 1.28 (t, 3H), 2.05 (m, 2H), 2.64 (s, 3H), 2.71-2.86 (m, 12H), 3.48 (m, 1H), 4.21 (q, 2H), 5.27-5.49 (m, 12H); MS (electrospray): 441.2 [M+Na]$^+$.

Step 2

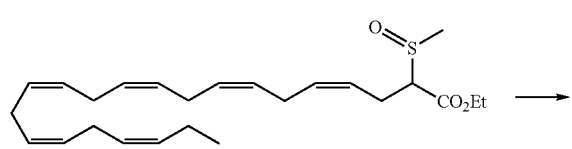

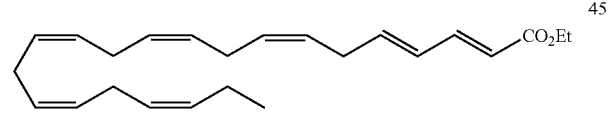

Ethyl (all-Z)-2-methanesulfinyl-docosa-4,7,10,13,16,19-hexaenoate (PRB-66, 0.68 g, 1.62 mmol) was dissolved in dry toluene (40 mL) and added CaCO$_3$ (0.16 g, 1.62 mmol). This mixture was stirred at 105° C. under inert atmosphere for three hours, cooled, diluted with heptane (50 mL) and washed with 1M HCl (50 mL) and brine (50 mL). The organic layer was dried (Na$_2$SO$_4$) and purified by flash chromatography (heptane:EtOAc 97:3) to afford 0.38 g (66%) of the title compound 14 as a pale yellow oil. $^1$H-NMR (200 MHz, CDCl$_3$): δ 0.95 (t, J 7.51, 3H), 1.25 (t, J 7.13, 3H), 2.05 (quint, J 7.35, 2H), 2.76-2.88 (m, 8H), 3.06 (t, J 7.25, 2H), 4.19 (q, J 7.13, 2H), 5.28-5.44 (m, 10H), 5.70-5.79 (m, 1H), 5.87 (d, J 15.22, 1H), 6.12 (dt, J 11.53, 0.71, 1H), 7.53-7.67 (ddd, J 15.24, J 11.61, J 1.02, 1H); $^{13}$C-NMR (75 MHz, CDCl$_3$): δ 14.20, 14.24, 20.49, 25.48, 25.57, 25.59, 25.62, 26.50, 60.23, 121.80, 126.45, 126.58, 126.96, 127.68, 127.79, 127.92, 128.26, 128.43, 128.50, 129.40, 131.94, 138.53, 138.86, 167.01; MS (electrospray): 377.2 [M+Na]$^+$.

EXAMPLE 18

(2E,4E,7Z,10Z,13Z,16Z,19Z)-docosa-2,4,7,10,13,16,19-heptaenoic acid (15)

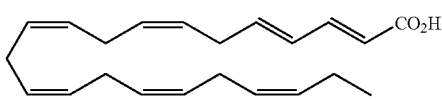

Ethyl (2E,4E,7Z,10Z,13Z,16Z,19Z)-docosa-2,4,7,13,16,19-heptaenoate (14), (0.26 g, 0.73 mmol) was dissolved in EtOH (10 mL) and added a mixture of LiOH (0.25 g, 5.9 mmol) in water (2.5 mL). The mixture was stirred at ambient temperature under inert atmosphere for 17 hours, added water (20 mL) and 1M HCl until pH=1. This mixture was extracted twice with heptane (20 mL) and the organic layer was dried (Na$_2$SO$_4$). Purification by flash chromatography (heptane:EtOAc 2:1 then 1:1) afforded 0.050 g (21%) of the title compound 15 as a colourless oil. $^1$H-NMR (200 MHz, CDCl$_3$): δ 0.95 (t, J 7.54, 3H), 2.05 (quint, J 7.51, 2H), 2.76-2.88 (m, 9H), 3.06 (t, 2H), 5.31-5.43 (m, 10H), 5.84-5.91 (m, 1H), 5.88 (d, J 15.17, 1H), 6.16 (dt, J 11.36, 0.70, 1H), 7.63-7.77 (ddd, J 15.21, 11.66, 0.90, 1H); MS (electrospray): 325.1 [M−H]$^−$.

EXAMPLE 19

(2E,4E,7Z,10Z,13Z,16Z,19Z)-docosa-2,4,7,10,13,16,19-heptaen-1-ol (16)

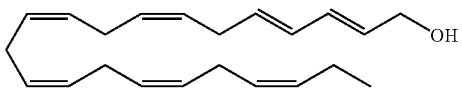

Ethyl (2E,4E,7Z,10Z,13Z,16Z,19Z)-docosa-2,4,7,10,13,16,19-heptaenoate (14) (0.12 g, 0.34 mmol) was dissolved in dry THF (3 mL) and added dropwise to a stirred suspension of LAH (0.013 g, 0.35 mmol) in dry THF (7 mL) at 0° C. The mixture was stirred at 0° C. for 45 minutes, added saturated NH$_4$Cl (5 mL) and filtered through a short pad of celite. The celite was washed with water (10 mL) and heptane (10 mL) and the combined aqueous layer was extracted with heptane (10 mL). The combined organic layer was dried (MgSO$_4$) and purified by flash chromatography (heptane:EtOAc 7:1). This afforded 0.070 g (66%) of the title compound 16 as colourless oil.

$^1$H-NMR (200 MHz, CDCl$_3$): δ 0.95 (t, J 7.52, 3H), 2.05 (quint, J 7.34, 2H), 2.76-2.91 (m, 8H), 2.96 (m, 2H), 4.20 (d, J 5.67, 2H), 5.28-5.46 (m, 11H), 5.78-5.87 (dt, J 15.12, 5.80, 1H), 6.00 (t, J 10.81, 1H), 6.52 (dd, J 15.12, 11.05, 1H); $^{13}$C-NMR (50 MHz, CDCl$_3$): δ 14.26, 20.55, 22.68, 25.53, 25.65, 26.08, 31.87, 63.49, 126.37, 127.00, 127.60, 127.86, 127.91, 128.02 (2 signals), 128.30 (2 signals), 128.59, 130.40, 132.05, 132.32 (one signal hidden); MS (electrospray): 335.2 [M+Na]+.

EXAMPLE 20

Ethyl (2E,4E,8Z,11Z,14Z,17Z)-2-methyl-icosa-2,4,8,11,14,17-hexaenoate (10)

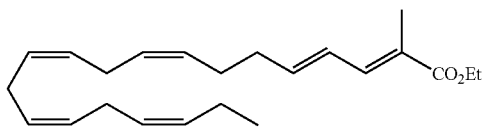

Triethyl 2-phosphonopropionate (458 μl, 2.13 mmol) was added to a suspension of sodium hydride (88 mg, 60% dispersion in mineral oil, 2.2 mmol) in dry THF (6 ml) at 0° C. After 50 minutes at 0° C. the mixture was cooled to −40° C. and (2E,6Z,9Z,12Z,15Z)-octadeca-2,6,9,12,15-pentaenal (500 mg, 1.94 mmol) in THF (1 ml) was added. The mixture was stirred for 60 minutes at −40° C. to −20° C. A saturated aqueous NH$_4$Cl solution of was added and the phases were separated. The aqueous phase was extracted with diethylether. The combined organic phases were washed with brine, water and dried (MgSO$_4$). Evaporation of the solvents under reduced pressure gave the ester 10.

EXAMPLE 21

(2E,4E,8Z,11Z,14Z,17Z)-2-methyl-icosa-2,4,8,11,14,17-hexaenoic acid (11)

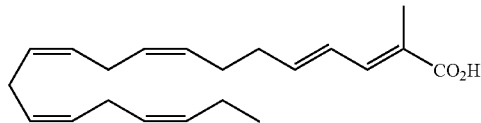

To a solution of ethyl (2E,4E,8Z,11Z,14Z,17Z)-2-methyl-icosa-2,4,8,11,14,17-hexaenoate (10) in methanol was added an aqueous solution of KOH (8 equiv.) and the mixture was heated to 60-70° C. for 2 hrs. The solution was cooled, water was added and the mixture acidified. The mixture was then extracted with ethyl acetate. The combined organic phases were washed with water and dried (MgSO$_4$). Evaporation of the solvents under reduced pressure followed by flash chromatography on silica gel (8:2 hexane-EtOAc) gave the acid 11. δ$_H$(300 MHz): 0.96 (t, J 7.5, 3H, CH$_3$), 1.91 (d, J 0.75, 3H, CH$_3$), 2.08 (m, 2H), 2.2-2.4 (m, 4H), 2.7-2.9 (m, 6H), 5.2-5.5 (m, 8H), 6.11 (dt, J 15.0, J 6.5, 1H), 6.37 (dd, J 15.0, J 11.3, 1H), 7.26 (br d, J 11.3, 1H); δ$_c$(75 MHz) 12.16, 14.24, 20.53, 25.52, 25.61, 25.67, 26.57, 33.24, 124.44, 126.34, 126.97, 127.82, 128.04, 128.21, 128.54, 128.70, 128.74, 132.01, 140.79, 143.47, 174.28.

EXAMPLE 22

Ethyl (2E,4E,8Z,11Z,14Z,17Z)-2-ethyl-icosa-2,4,8,11,14,17-hexaenoate 17

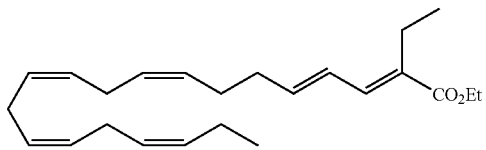

A suspension of NaH (60% in mineral oil, 0.11 g, 2.79 mmol) in dry THF (15 mL) was given 0° C. under inert atmosphere and triethyl 2-phosphonobutyrate (0.66 mL, 2.79 mmol) was added dropwise. The mixture was stirred at 0° C. for ten minutes, added a solution of (2E,6Z,9Z,12Z,15Z)-octadeca-2,6,9,12,15-pentaenal (0.48 g, 1.86 mmol) in dry THF (5 mL) and stirred at 0° C. for another 30 minutes. The mixture was diluted with diethyl ether (30 mL), washed with water (30 mL) and dried (Na$_2$SO$_4$). Purification by flash chromatography (heptane:EtOAc 98:2) afforded 0.39 g (59%) of ester 17 (2E:2Z=9:1) as colourless oil.

This product mixture was purified a second time, this time by flash chromatography using a flash-instrument (heptane:EtOAc 99:1). This afforded 0.095 g (14%) of pure ethyl-(2E,4E,8Z,11Z,14Z,17Z)-2-ethyl-eicosa-2,4,8,11,14,17-hexaneoate (17) as a colourless oil. $^1$H-NMR (200 MHz, CDCl$_3$): δ 0.95 (t, J 7.53, 3H), 1.01 (t, J 7.44, 3H), 1.28 (t, J 7.12, 3H), 1.98-2.15 (m, 2H), 2.15-2.29 (m, 4H), 2.38 (q, J 7.44, 2H), 2.70-2.90 (m, 6H), 4.18 (q, J 7.11, 2H), 5.22-5.44 (m, 8H), 5.98-6.12 (m, 1H), 6.28-6.41 (dd, J 11.20, J 11.20, 1H), 7.09 (d, J 11.17, 1H); $^{13}$C-NMR (50 MHz, CDCl$_3$): δ 14.22, 14.30, 20.24, 20.54, 25.52, 25.61, 25.67, 26.65, 33.18, 60.30, 126.05, 126.98, 127.84, 128.09, 128.17, 128.54, 128.64, 128.82, 131.86, 132.01, 137.93, 142.14, 173.05, (one signal hidden); MS (electrospray): 379.2 [M+Na]+.

A small amount (20 mg, 3%) of ethyl (2Z,4E,8Z,11Z,14Z,17Z)-2-ethyl-eicosa-2,4,8,11,14,17-hexaneoate (35) was also isolated as a colourless oil. $^1$H-NMR (200 MHz, CDCl$_3$): δ 0.95 (t, J 7.52, 3H), 1.04 (t, J 7.36, 3H), 1.29 (t, J 7.14, 3H), 1.95-2.12 (m, 2H), 2.15-2.25 (m, 6H), 2.27 (q, J 7.36, 2H), 2.75-2.90 (m, 6H), 4.18 (q, J 7.14, 2H), 5.22-5.44 (m, 8H), 5.77-5.95 (m, 1H), 6.29-6.34 (dd, J 0.82, 11.09, 11H), 6.97-7.11 (dd, J 11.10, 11.08, 1H).

EXAMPLE 23

(2E,4E,8Z,11Z,14Z,17Z)-2-ethyl-icosa-2,4,8,11,14,17-hexaenoic acid (18)

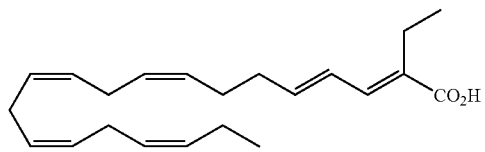

Ethyl-(2E,4E,8Z,11Z,14Z,17Z)-2-ethyl-eicosa-2,4,8,11,14,17-hexaneoate (17) (0.040 g, 0.112 mmol) was dissolved in ethanol (4 mL) and added a solution of LiOH×H$_2$O (0.038 g, 0.898 mmol) in water (1 mL). The mixture was stirred at ambient temperature for 15 hours, followed by five hours at 70° C. The mixture was cooled, added 1M HCl until pH=1 and diluted with water (2 mL). The mixture was extracted twice with heptane (10 mL) and the combined organic extracts were dried (Na$_2$SO$_4$). Purification by flash chromatography (heptane:EtOAc 95:5 then 4:1) afforded 0.028 g (76%) of the title compound as a pale yellow oil. $^1$H-NMR (200 MHz, CDCl$_3$): δ 0.90-1.07 (2×t, 6H), 2.00-2.10 (m, 2H), 2.20-2.30 (m, 4H), 2.35-2.50 (q, 2H), 2.75-2.90 (m, 6H), 5.27-5.44 (m, 8H), 6.05-6.20 (m, 1H), 6.30-6.43 (m, 1H), 7.50-7.70 (m, 1H); MS (electrospray): 327.2 [M−H]$^−$.

EXAMPLE 24

(2E,4E,8Z,11Z,14Z,17Z)-2-ethyl-icosa-2,4,11,14,17-hexaen-1-ol (19)

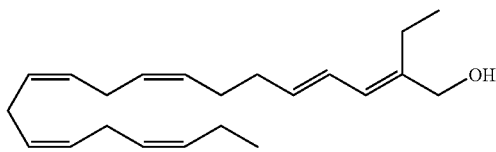

A suspension of LAH (0.007 g, 0.168 mmol) in dry THF (2 mL) was cooled to 0° C. under inert atmosphere. To this suspension was added dropwise to a solution of ethyl-(2E,4E,8Z,11Z,14Z,17Z)-2-ethyl-eicosa-2,4,8,11,14,17-hexaneoate (17) (E:Z=9:1, 0.060 g, 0.168 mmol). The mixture was stirred at 0° C. for two hours, followed by stirring at ambient temperature for 17 hours, and then saturated NH$_4$Cl (5 mL) was added. The mixture was extracted twice with heptane (10 mL) and the combined organic extracts were washed with brine (10 mL) and dried (Na$_2$SO$_4$).

Purification by flash chromatography (heptane:EtOAc 6:1) afforded 0.030 g (57%) of (2E,4E,8Z,11Z,14Z,17Z)-2-ethyl-eicosa-2,4,8,11,14,17-hexaen-1-ol (19) as a colourless oil. $^1$H-NMR (200 MHz, CDCl$_3$): δ 0.95 (t, J 7.5, 3H), 1.02 (t, J 7.5, 3H), 1.98-2.09 (m, 2H), 2.12-2.26 (m, 6H), 2.77-2.89 (m, 6H), 4.07 (s, 2H), 5.27-5.41 (m, 8H), 5.61-5.75 (m, 1H), 5.96 (d, J 10.9, 1H), 6.20-6.34 (dd, J 10.9, 14.9, 1H); $^{13}$C-NMR (50 MHz, CDCl$_3$): δ 13.46, 14.24, 20.53, 21.52, 25.51, 25.59, 25.67, 27.11, 32.89, 66.63, 124.91, 125.95, 127.00, 127.90, 128.07, 128.25 (2 signals), 128.51, 129.28, 132.01, 134.33, 141.07; MS (electrospray): 337.2 [M+Na]$^+$.

A small amount of (2Z,4E,8Z,11Z,14Z,17Z)-2-ethyl-eicosa-2,4,8,11,14,17-hexaen-1-ol (36, 0.004 g, 7%) was also isolated as a colourless oil. $^1$H-NMR (200 MHz, CDCl$_3$): δ 0.95 (t, J 7.5, 3H), 1.05 (t, J 7.5, 3H), 1.95-2.09 (m, 2H), 2.14-2.24 (m, 6H), 2.76-2.84 (m, 6H), 4.23 (s, 2H), 5.23-5.45 (m, 8H), 5.59-5.74 (m, 1H), 5.89 (d, J 10.9, 1H), 6.29-6.42 (dd, J 10.9, 16.8, 1H).

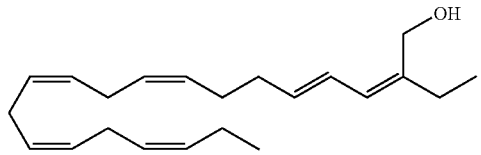

EXAMPLE 25

Ethyl (2E/Z,4E,13Z,16Z,19Z)-3-methyl-docosa-2,4,13,16,19-pentaenoate (37)

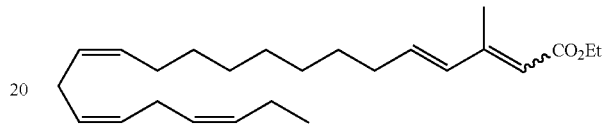

Triethyl-3-methyl-4-phosphono-2-butenoate (0.32 mL, 1.09 mmol) was dissolved in dry THF (12 mL) and dry DMPU (3 mL) and given 0° C. under inert atmosphere. n-BuLi (0.68 ml, 1.09 mmol) was added dropwise, the mixture was stirred at 0° C. for 20 minutes and then given −78° C. The mixture was stirred at −78° C. for five minutes, (all-Z)-octadeca-9,12,15-trienal (0.22 g, 0.84 mmol) in dry THF (3 mL) was added dropwise and the mixture was allowed to slowly reach −10° C. over 80 minutes. Saturated NH$_4$Cl (20 mL) was added and the mixture was extracted twice with heptane (30 mL). The organic layer was dried (Na$_2$SO$_4$) and purified by flash chromatography (heptane:EtOAc 98:2). This afforded 0.31 g (95%) of the title compound as a 1:1 mixture of the E- and Z-isomer as colourless oils. $^1$H-NMR (200 MHz, CDCl$_3$): δ 0.95 (t, 6H), 1.20-1.50 (m, 26H), 1.95 (s, 3H), 1.98-2.35 (m, 12H), 2.40 (s, 3H), 2.78 (m, 8H), 4.13 (q, 4H), 5.25-5.40 (m, 12H), 5.57 (s, 1H), 5.66 (s, 1H), 6.04-6.16 (m, 2H), 7.54 (d, 1H); MS (electrospray): 395.3 [M+Na]$^+$.

EXAMPLE 26

(2E,4E,13Z,16Z,19Z)-3-methyl-docosa-2,4,13,16,19-pentaenoic acid (20)

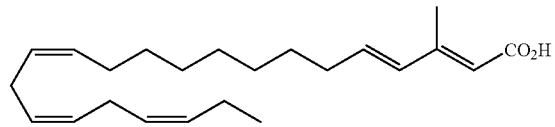

Ethyl (2E/Z,4E,13Z,16Z,19Z)-3-methyl-docosa-2,4,13,16,19-pentaenoate (37) (2E:2Z=1:1, 0.30 g, 0.81 mmol) was dissolved in EtOH (10 mL) and added LiOH×H$_2$O (0.27 g, 6.44 mmol) in water (2.5 mL). The mixture was stirred at 70° C. under inert atmosphere for two hours, cooled and added 1M HCl until pH=1. The mixture was extracted twice with heptane (30 mL) and the combined organic layer was dried (Na$_2$SO$_4$). Purification by flash chromatography (heptane:EtOAc 4:1) afforded 0.090 g (32%) of the title compound as a colourless oil. $^1$H-NMR (200 MHz, CDCl$_3$): δ 0.95 (t, 3H), 1.25-1.50 (m, 10H), 1.98-2.15 (m, 7H), 2.20-2.30 (m, 2H), 2.79 (m, 4H), 5.27-5.42 (m, 6H), 5.61 (s, 11H), 6.11-6.21 (dt, J 15.8, J 7.0, 1H), 7.53 (d, J 15.8, 1H), 11.70 (br s, 11H). $^{13}$C-NMR (75 MHz, CDCl$_3$): δ 14.25, 20.53, 21.33, 25.51, 25.60, 27.21, 29.06, 29.20, 29.26, 29.36, 29.61, 33.41, 115.01, 127.11, 127.59, 127.66, 128.24, 128.26, 130.32, 131.92, 140.31, 153.89, 171.81; MS (electrospray): 345.3 [M+H]$^+$, 367.3 [M+Na]$^+$.

EXAMPLE 27

(2E,4E,13Z,16Z,19Z)-3-methyl-docosa-2,4,13,16,19-pentaenoic acid (21)

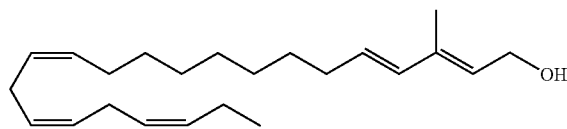

A suspension of LAH (0.011 g, 0.282 mmol) in dry THF (8 mL) was given 0° C. under inert atmosphere and a solution of ethyl (2E/Z,4E,13Z,16Z,19Z)-3-methyl-docosa-2,4,13,16,19-pentaenoate (2E:2Z=1:1, 0.10 g, 0.268 mmol) in dry THF (2 mL) was added dropwise. The mixture was stirred at 0° C. for one hour, then at ambient temperature for 30 minutes and then added 10% NH$_4$Cl (10 mL). The mixture was extracted twice with heptane (20 mL) and the combined organic extracts were washed with brine (20 mL) and dried (Na$_2$SO$_4$). Purification by flash chromatography (heptane:EtOAc 9:1) afforded 0.030 g (34%) of (2E,4E,13Z,16Z,19Z)-3-methyl-docosa-2,4,13,16,19-pentaen-1-ol (21) as a colourless oil. $^1$H-NMR (200 MHz, CDCl$_3$): δ 0.96 (t, J 7.5, 3H), 1.20-1.40 (m, 10H), 1.76 (s, 3H), 1.99-2.13 (m, 6H), 2.76-2.82 (m, 4H), 4.24 (d, J 6.93, 2H), 5.26-5.41 (m, 6H), 5.54 (t, J 6.9, 11H), 5.60-5.75 (dt, J 15.6, 6.9, 11H), 6.05 (d, J 15.6, 1H); $^{13}$C-NMR (50 MHz, CDCl$_3$): δ 12.59, 14.26, 20.54, 25.51, 25.61, 27.22, 29.18, 29.23, 29.38, 29.48, 29.62, 32.83, 59.35, 127.11, 127.66 (2 signals), 128.26 (2 signals), 130.34, 130.66, 131.94, 133.88, 136.62; MS (electrospray): 353.3 [M+Na]$^+$.

(2Z,4E,13Z,16Z,19Z)-3-methyl-docosa-2,4,13,16,19-pentaen-1-ol (38) was isolated as a colourless oil (0.04 g, 45%)

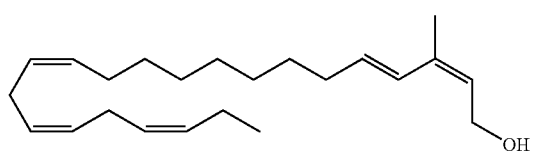

$^1$H-NMR (200 MHz, CDCl$_3$): δ 0.96 (t, J 7.5, 3H), 1.20-1.45 (m, 10H), 1.83 (s, 3H), 1.98-2.15 (m, 6H), 2.76-2.82 (m, 4H), 4.25 (d, J 7.19, 2H), 5.26-5.49 (m, 7H), 5.68-5.83 (dt, J 15.50, 6.95, 1H), 6.39 (d, J 15.5, 1H); $^{13}$C-NMR (50 MHz, CDCl$_3$): δ 14.07, 20.59, 22.68, 25.51, 25.60, 27.22, 29.01, 29.22, 29.39, 29.63, 31.87, 33.24, 58.38, 126.06, 126.21, 127.11, 127.67, 128.25 (2 signals), 130.32, 131.93, 133.16, 135.76; MS (electrospray): 353.3 [M+Na]$^+$.

EXAMPLE 28

Ethyl (2Z/2E,4E,13Z,16Z,19Z)-2-ethyl-docosa-2,4,13,16,19-heptaenoate (22)

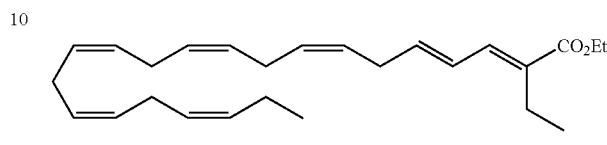

Step 1:

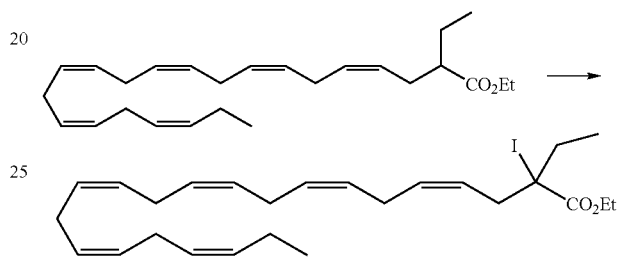

Diisopropyl amine (0.84 mL, 5.98 mmol) was dissolved in dry THF (20 mL) and cooled to 0° C. under inert atmosphere. n-BuLi (1.6 M in hexanes, 3.58 mL, 5.72 mmol) was added dropwise, the mixture stirred at 0° C. for ten minutes and then cooled to −78° C. A mixture of ethyl (all Z)-2-ethyl-docosa-4,7,10,13,16,19-hexaenoate (2.00 g, 5.20 mmol) in dry THF (20 mL) was added dropwise over 20 minutes, the resulting dark green solution was stirred at −78° C. for ten minutes and then added a solution of I$_2$ (1.98 g, 7.80 mmol) in dry THF (10 mL). The mixture was then allowed to reach ambient temperature over 80 minutes, portioned between saturated Na$_2$SO$_3$ (40 mL) and heptane (40 mL). The aqueous layer was extracted with heptane (40 mL) and the combined organic extracts were washed with 1M HCl (40 mL) and dried (Na$_2$SO$_4$). Purification by flash chromatography (heptane: EtOAc 98:2) afforded 1.70 g (64%) of ethyl (all-Z)-2-ethyl, 2-iodo-docosa-4,7,10,13,16,19-hexaenoate. ($^1$H-NMR (200 MHz, CDCl$_3$): δ 0.88-0.99 (m, 6H), 1.19-1.31 (m, 4H), 1.98-2.19 (m, 4H), 2.75-2.95 (m, 12H), 5.28-5.45 (m, 12H); MS (electrospray): 533.2 [M+Na]$^+$.

Step 2:

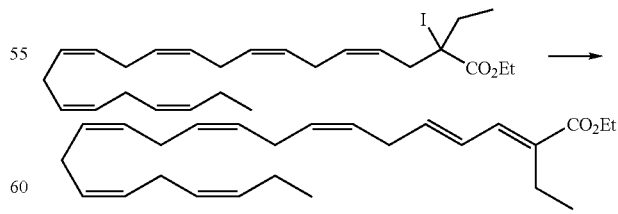

Ethyl (all-Z)-2-ethyl-2-iodo-docosa-4,7,10,13,16,19-hexaenoate (1.55 g, 3.04 mmol) was dissolved in dry diethyl ether (50 mL) under inert atmosphere and DBU (0.45 mL, 3.04 mmol) was added. The mixture was stirred at ambient temperature for 23 hours, diluted with heptane (50 mL) and the organic layer was washed with saturated NH$_4$Cl (50 mL). The aqueous layer was extracted with heptane (40 mL) and the combined organic extracts were washed with 0.1M HCl (40 mL) and dried (Na$_2$SO$_4$). Purification by flash chromatography (heptane:EtOAc 98:2) afforded 1.16 g (quant) of the title compound 22 (E/Z=4:1) as colourless oil. $^1$H-NMR (200 MHz, CDCl$_3$):

E-isomer: δ 0.84-0.99 (2×t, 6H), 1.19-1.28 (t, 3H), 2.01-2.09 (m, 4H), 2.76-2.95 (m, 10H), 4.11 (q, 2H), 5.20-5.45 (m, 10H), 5.55-5.75 (m, 1H), 6.00-6.20 (m, 2H).

Z-isomer: δ 0.84-0.99 (2×t, 6H), 1.19-1.28 (t, 3H), 1.70-1.90 (m, 2H), 2.01-2.09 (m, 2H), 2.76-2.95 (m, 101H), 4.23 (q, 2H), 5.20-5.45 (m, 111H), 5.55-5.75 (m, 1H), 6.10-6.20 (m, 1H).

MS (electrospray): 405.3 [M+Na]$^+$.

EXAMPLE 29

(2E,4E,13Z,16Z,19Z)-2-ethyl-docosa-2,4,13,16,19-heptaen-1-ol (23)

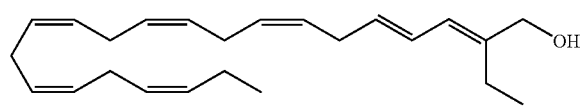

A suspension of LAH (0.044 g, 1.15 mmol) in dry THF (10 mL) under inert atmosphere was given 0° C. and a mixture of ethyl (2E/Z,4E,7Z,10Z,13Z,16Z,19Z)-2-ethyl-docosa-2,4,7,10,13,16,19-heptaenoate (2E:2Z=1:1, 0.40 g, 1.05 mmol) in dry THF (5 mL) was added dropwise. The mixture was stirred at 0° C. for one hour, then at ambient temperature for one hour and quenched by addition of saturated NH$_4$Cl (10 mL). The mixture was extracted twice with heptane (20 mL) and the combined organic extracts were washed with brine (20 mL) and dried (Na$_2$SO$_4$). Purification by flash chromatography (heptane:EtOAc 9:1) afforded 0.110 (31%) of (2E,4E,7Z,10Z,13Z,16Z,19Z)-2-ethyl-docosa-2,4,7,10,13,16,19-heptaen-1-ol (23) as a colourless oil. $^1$H-NMR (200 MHz, CDCl$_3$): δ 0.84-0.99 (2×t, 6H), 2.01-2.20 (m, 4H), 2.77-2.90 (m, 8H), 2.92-2.98 (m, 2H), 3.50 (m, 2H), 5.28-5.41 (m, 10H), 6.00-6.45 (m, 3H); $^{13}$C-NMR (50 MHz, CDCl$_3$): δ 11.64, 14.25, 20.54, 24.00, 25.52, 25.62, 25.63, 26.16, 47.80, 65.78, 126.80, 126.99, 127.70, 127.83, 127.97, 128.30, 128.50, 128.56, 128.71, 130.03, 132.02, 132.68, 133.09, 135.51; MS (electrospray): 363.2 [M+Na]$^+$.

0.040 g (11%) of (2Z,4E,7Z,10Z,13Z,16Z,19Z)-2-ethyl-docosa-2,4,7,10,13,16,19-heptaen-1-ol (39) was also isolated as a colourless oil. $^1$H-NMR (200 MHz, CDCl$_3$): δ 0.86-0.99 (2×t, 6H), 2.02-2.19 (m, 4H), 2.76-2.90 (m, 10H), 3.53 (m, 2H), 5.23-5.44 (m, 13H); $^{13}$C-NMR (50 MHz, CDCl$_3$): δ 11.38, 14.25, 20.54, 23.41, 25.52, 25.63 (2 signals), 28.51, 42.58, 65.23, 126.99, 127.86, 128.10, 128.12, 128.14, 128.16, 128.26 (2 signals), 128.56, 129.09, 132.03, (3 signals hidden).

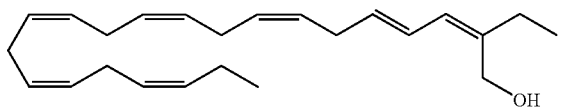

EXAMPLE 30

Ethyl (2E,4E,6E,10Z,13Z,16Z,19Z)-3-methyl-docosa-2,4,6,10,13,16,19-heptaenoate (24)

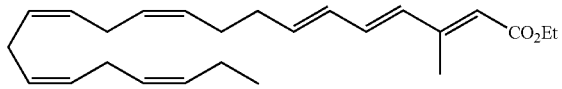

A solution of triethyl 3-methyl-4-phosphono-2-butenoate (485 μl, 1.96 mmol) in a 5:1 mixture of anhydrous THF-DMPU (20 ml) was cooled to 0° C., and n-BuLi (2.5 M in hexane, 760 μl, 1.90 mmol) was added. The mixture was stirred for 0° C. for 20 min and then cooled to −78° C. A solution of (2E,6Z,9Z,12Z,15Z)-octadeca-2,4,6,10,13,16,19-pentaenal in THF (2 ml) was added, and the reaction mixture was stirred at −78° C. for an hour. The mixture was then allowed to warm to 0° C. during an hour. Then a saturated aqueous NH$_4$Cl solution was added and the phases were separated. The aqueous phase was extracted with ethyl acetate. The combined organic phases were washed with water and dried (MgSO$_4$). Evaporation of the solvents under reduced pressure followed by flash chromatography on silica: gel (95:5 hexane-EtOAc) gave the ester (120 mg).

EXAMPLE 31

(2E,4E,6E,10Z,13Z,16Z,19Z)-3-methyl-docosa-2,4,6,10,13,16,19-heptaenoic acid (25)

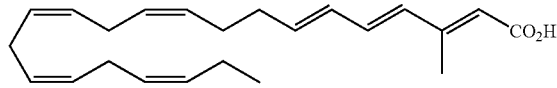

To a solution of the ester in methanol was added an aqueous solution of KOH (8 equiv.) and the mixture was heated to 60-70° C. for 2 hrs. The solution was cooled, water was added and the mixture acidified. The mixture was then extracted with ethyl acetate. The combined organic phases were washed with water and dried (MgSO$_4$). Evaporation of the solvents under reduced pressure gave the acid. δ$_H$(300 MHz): 0.95 (t, J 7.5, 3H, CH$_3$), 2.05 (2H, m), 2.15-2.25 (4H, m), 2.28 (d, J 0.93, 3H), 2.7-2.9 (m, 6H), 5.2-5.5 (m, 8H), 5.75 (bs, 1H), 5.85-5.95 (m, 1H), 6.10-6.25 (2H, m), 6.60 (dd, J 15.3, J 10.4, 1H); δ$_c$(75 MHz) 13.91, 14.27, 20.55, 25.54, 25.63, 25.69, 26.76, 32.92, 117.70, 126.99, 127.86, 128.13, 128.17, 128.56, 128.60, 128.92, 130.48, 132.05, 133.54, 135.78, 139.02, 155.21, 172.15.

Biological Activity

TEST EXAMPLE 1

Activation and Binding to Ligand Binding Domain of Human PPARα, γ, δ and RXRα

The activation and binding of novel compounds to the ligand binding domain (LBD) of the nuclear receptors PPARα, PPARγ, PPARδ or RXRα in human (h) were measured.

To study this, a transient transfection gene/cell system was used Chimeric constructs were made from the human LBD-sThe DBD of PPARα, PPARγ, PPARδ or RXRα were substituted with GAL4DBD. Following plasmid constructs were made: pSG5-GAL4-hPPARα, pSG5-GAL4-hPPARδ, pSG5-GAL4-hPPARδ and pSG5-GAL4-hRXRα. The plasmids, .

chimera's and the reporter LUC, were transfected into COS-1 cells and luciferase protein was analyzed as described in methods.

PPARα ligand (Wy 14.643), a RXRα ligand (9-cis-retinoic acid) and a PPARγ ligand: Rosiglitazone and PPARδ ligand: bezafibrate were used as positive controls.

Method:
Fatty Acids/Ligands

Wy-14.643, 9-cis-retinoic acid (9-cis-RA) or Rosiglitazone and novel compounds (stock solutions) were solubilized to 0.1 M final concentration in DMSO. Then, solubilized to 10 mM in DMSO and stored in 1.5 ml tubes (homopolymer, plastic tubes) flushed with argon and stored at −20° C.

Cell Cultures

COS-1 cells (ATCC no. CRL 1650) were cultured in DMEM supplemented with L-glutamine (2 MM), penicillin (50 U/ml), streptomycin (50 μG/mL), fungizone (2.5 μg/mL), and 10% inactivated FBS. The cells were incubated at 37° C. in a humidified atmosphere of 5% $CO_2$ and 95% air and used for transient transfections. Every third day, the cells in each flask were split into new flasks containing fresh media.

Transfection

Cells (1.5×1 mil) were plated in 30 mm tissue dishes (six-well plates), 1 d before transfection. Transient transfection by lipofectamin 2000 was performed as described (Invitrogen, Carlsbad, Calif.). Each well received 990 ng plasmid: 320 ng reporter ((UAS)5-tk-LUC (UAS=upstream activating sequence and LUC=luciferase), 640 ng pGL3 basic (empty vector) and 30 ng expression plasmid of pSG5-GAL4-hPPARα, pSG5-GAL4-hPPARγ, pSG5-GAL4-hPPARδ or pSG5-GAL4-hRXRα, which are chimera expression constructs containing the ligand binding domain (LBD) of human (h) PPARα, PPARγ, PPARδ and RXRα. The LPGs, Wy 14.643, 9cisRA or BRL (10 μM) and DMSO (control) was added to the media 5 h after transfection. Transfected cells were maintained for 24 h before lysis by reporter lysis buffer. Binding of LPGs or ligands to the LBD of PPAR activates GAL4 binding to UAS, which in turn stimulates the tk promoter to drive luciferase expression. Luciferase activity was measured using a luminometer (TD-20/20 luminometer; Turner Designs, Sunnyvale, Calif.) and normalized against protein content.

Results:

The results according to table 1, shows that some of the novel compounds covered by the invention have the potential of being selective PPARα modulators/activators (Compound 4, 11 and 13). The results also show that some of the compounds are PPAR pan modulators/activators in addition to being a RXRα ligand (Compound 25).

TEST EXAMPLE 2

Inhibition of NF-κB in Human Monocytic Cell Lines

Method
Substances

The novel compounds and DHA were solubilized to 12.5 μM in DMSO flushed with argon and stored at −20° C. Dexamethasone 10 μM in DMSO was used as positive control.

Cell Cultures

U937-3xkB-LUC cells, (Carlsen, *J. Immun*, 2002), were cultured in RPMI-1640 medium with L-glutamine (2 nM), penicillin (50 U/ml), streptomycin (50 mg/ml), hygromycin (75 ug/ml), 10% Fetal Bovine Serum at 37° C. and 5% $CO_2$. In the Cells were seeded in 24-well plates wherein 1% Fetal Bovin Serum was added to the medium. NF-κB activity was induced by lipopolysaccharide (LPS) (1 ug/ml) or human TNF-α (10 ng/ml). Cell viability was measured by trypan blue staining.

Luciferase Activity Assay

Luciferase activity was measured by imaging with a IVIS Imaging System from Xenogen Corp., USA. The Luminescence was detected after 1 min. and 5 min after addition of 0.2 mg d-luciferin per. ml cell medium. Number of photons in each well pr. second was calculated using Living Image Software (Xenogen Corp., USA).

Results

Some of the compounds covered by the invention are potent inhibitors of the NF-κB pathway (Compound 13 and 25). These two compounds have similar inhibitory potency as Dexamethasone, see FIG. 1.

The invention claimed is:
1. A lipid compound of formula (I):

$$\text{(I)}$$

wherein
n=0, 1, or 2;
$R_1$ and $R_2$ are the same or different and are chosen from a hydrogen atom, an alkyl group, a halogen atom, and an alkoxy group;

TABLE 1

Luciferase activation (fold activation) as a result of ligand binding of novel compounds at 10 μM concentration, to the ligand binding domain of human PPARα, γ and δ in addition to human RXRα.

| Compound | hPPARα | hPPARγ | hPPARδ | hRXRα |
|---|---|---|---|---|
| Negative control | 1.00 | 1.00 | 1.00 | 1.00 |
| Wy14643 | 2.27 ± 0.04 | | | |
| 9-(Z)-retinoic acid | | | | 2.72 ± 0.32 |
| Bezafibrate | | | 0.99 ± 0.01 | |
| Rosiglitazone | | 13.27 ± 0.56 | | |
| DHA | 1.57 ± 0.19 | 1.86 ± 0.17 | 1.09 ± 0.01 | 0.83 ± 0.09 |
| 4 | 4.51 ± 0.52 | 1.56 ± 0.12 | 1.28 ± 0.08 | 0.90 ± 0.08 |
| 11 | 6.79 ± 0.21 | 1.67 ± 0.11 | 1.17 ± 00.20 | 0.84 ± 0.09 |
| 13 | 4.89 ± 0.31 | 1.63 ± 0.06 | 1.11 ± 0.16 | 0.81 ± 0.05 |
| 25 | 8.27 ± 0.81 | 4.32 ± 0.29 | 1.47 ± 0.38 | 1.57 ± 0.08 |

X is chosen from $COR_3$ and $CH_2OR_4$, wherein $R_3$ is chosen from a hydrogen atom, a hydroxy group, an alkoxy group, and an amino group, wherein when $R_3$ is hydroxy, X is optionally a carboxylic acid derivative; and $R_4$ is chosen from a hydrogen atom, an alkyl group, and an acyl group; and Y is an unsubstituted $C_9$ to $C_{21}$ alkene with at least one double bond having either E or Z configuration, wherein $R_1$ and $R_2$ are not both a hydrogen atom.

2. The lipid compound according to claim 1, of formula (II):

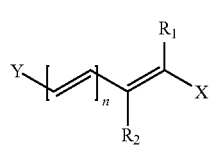

(II)

wherein
n=0, 1, or 2;
$R_1$ and $R_2$ are the same or different and are chosen from a hydrogen atom, an alkyl group, a halogen atom, and an alkoxy group;
X is chosen from $COR_3$ and $CH_2OR_4$, wherein $R_3$ is chosen from a hydrogen atom, a hydroxy group, an alkoxy group, and an amino group, wherein when $R_3$ is hydroxy, X is optionally a carboxylic acid derivative; and $R_4$ is chosen from a hydrogen atom, an alkyl group, and an acyl group; and
Y is an unsubstituted $C_9$ to $C_{21}$ alkene with at least one double bond having either E or Z configuration, wherein $R_1$ and $R_2$ are not both a hydrogen atom.

3. The lipid compound according to claim 1, wherein the carboxylic derivative is chosen from a phospholipid, a monoglyceride, a diglyceride, and a triglyceride.

4. The lipid compound according to claim 1, wherein $R_1$ and $R_2$ are the same or different and are chosen from a $C_1$-$C_7$ alkyl group, a $C_1$-$C_7$ alkoxy group, and a halogen atom.

5. The lipid compound according to claim 1, wherein $R_1$ and $R_2$ are the same or different and are chosen from a $C_1$-$C_3$ alkyl group, a $C_1$-$C_3$ alkoxy group, and a halogen atom.

6. The lipid compound according to claim 1, wherein $R_3$ is chosen from a $C_1$-$C_7$ alkoxy group and a hydroxy group.

7. The lipid compound according to claim 1, wherein $R_4$ is chosen from a $C_1$-$C_7$ alkyl group and a $C_1$-$C_7$ acyl group.

8. The lipid compound according to claim 1, wherein the double bond between the carbon atoms 2 and 3 is in the E-configuration.

9. The lipid compound according to claim 1, comprising a carbon-carbon double bond in the ω-3 position of Y.

10. The lipid compound according to claim 1, wherein $R_1$ and $R_2$ are the same or different and are chosen from a methyl group and an ethyl group.

11. The lipid compound according to claim 1, wherein $R_1$ and $R_2$ are different, and one is a $C_1$-$C_3$ alkoxy and the other one is a hydrogen.

12. The lipid compound according to claim 11, wherein the double bond between the carbon atoms 2 and 3 is in Z-configuration.

13. The lipid compound according to claim 1, wherein the halogen atom is fluorine.

14. The lipid compound according to claim 1, wherein Y is a $C_{14}$-$C_{19}$ alkene with 2-6 double bonds.

15. The lipid compound according to claim 14, wherein Y is a $C_{14}$-$C_{19}$ alkene with 2-6 methylene interrupted double bonds in Z configuration.

16. The lipid compound according to claim 1, wherein n=0, and Y is a $C_{13}$-$C_{19}$ alkene having 2-6 double bonds.

17. The lipid compound according to claim 1, wherein n=1, and Y is a $C_{11}$-$C_{17}$ alkene having 2-5 double bonds.

18. The lipid compound according to claim 1, wherein n=2, and Y is a $C_9$-$C_{16}$ alkene having 1-4 double bonds.

19. The lipid compound according to claim 1, wherein n=0, of formula (III):

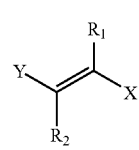

(III)

wherein the double bond between the carbon atoms 2 and 3 is in the E-configuration;
$R_1$ and $R_2$ are the same or different and are chosen from an alkyl group, a halogen atom, and an alkoxy group;
X is chosen from $COR_3$ and $CH_2OR_4$, wherein $R_3$ is chosen from a hydrogen atom, a hydroxy group, an alkoxy group, and an amino group, wherein when $R_3$ is hydroxy, X is optionally a carboxylic acid derivative; and $R_4$ is chosen from a hydrogen atom, an alkyl group, and an acyl group; and
Y is an unsubstituted $C_9$ to $C_{21}$ alkene with at least one double bond having either E or Z configuration.

20. The lipid compound according to claim 1, chosen from

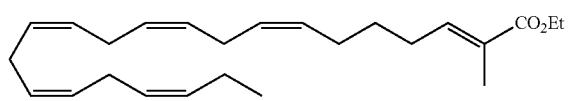

ethyl (2E,7Z,10Z,13Z,16Z,19Z) 2-methyl-docosa-2,7,10,13,16,19-hexaenoate,

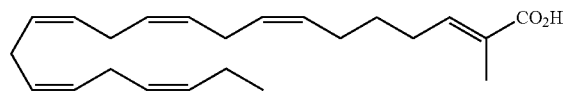

(2E,7Z,10Z,13Z,16Z,19Z)-2-methyl-docosa-2,7,10,13,16,19-hexaenoic acid,

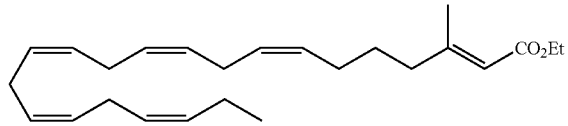

ethyl (2E,7Z,10Z,13Z,16Z,19Z) 3-methyl-docosa-2,7,10,13,16,19-hexaenoate,

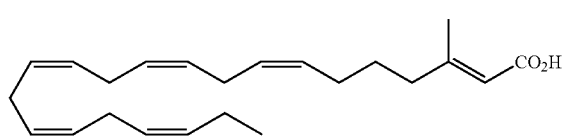

(2Z,7Z,10Z,13Z,16Z,19Z)-3-methyl-docosa-2,7,10,13,16,19-hexaenoic acid,

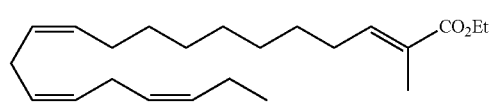

ethyl (2E,11Z,14Z,17Z)-2-methyl-eicosa-2,11,14,17-tetraenoate,

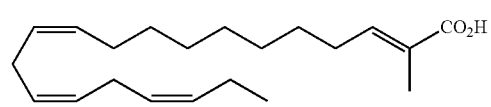

(2E,11E,14E,17E)-2-methyl-eicosa-2,11,14,17-tetraenoic acid,

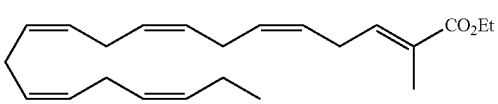

ethyl (2E,5Z,8Z,11Z,14Z,17Z)-2-methyl-icosa-2,5,8,11,14,17-hexaenoate,

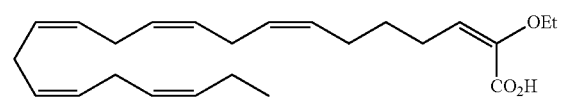

(2Z,7Z,10Z,13Z,16Z,19Z) 2-ethoxy-docosa-2,7,10,13,16,19-hexaenoic acid,

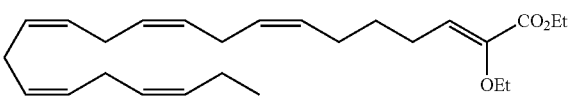

ethyl (2Z,7Z,10Z,13Z,16Z,19Z) 2-ethoxy-docosa-2,7,10,13,16,19-hexaenoate,

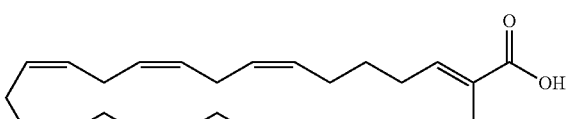

(2E,7Z,10Z,13Z,16Z,19Z) 2-ethyl-docosa-2,7,10,13,16,19-hexaenoic acid,

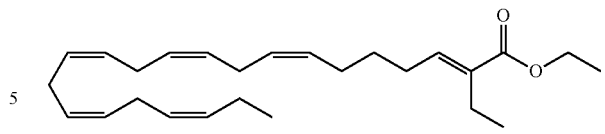

ethyl (2E,7Z,10Z,13Z,16Z,19Z) 2-ethyl-docosa-2,7,10,13,16,19-hexaenoate,

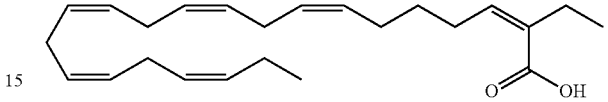

(2Z,7Z,10Z,13Z,16Z,19Z) 2-ethyl-docosa-2,7,10,13,16,19-hexaenoic acid,

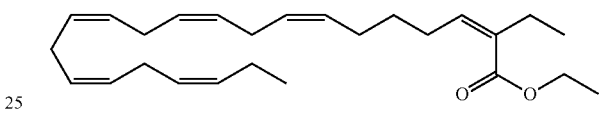

ethyl (2Z,7Z,10Z,13Z,16Z,19Z) 2-ethyl-docosa-2,7,10,13,16,19-hexaenoate,

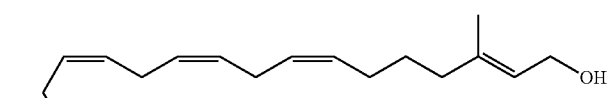

(2E,7Z,10Z,13Z,16Z,19Z) 3-methyl-docosa-2,7,10,13,16,19-hexaen-1-ol,

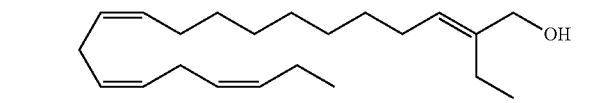

(2E,11Z,14Z,17Z) 2-ethyl-eicosa-2,11,14,17-tetraen-1-ol,

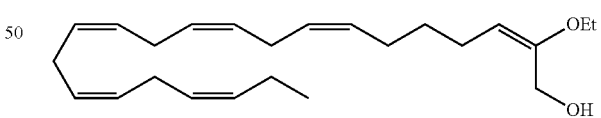

(2E,7Z,10Z,13Z,16Z,19Z) 2-ethoxy-docosa-2,7,10,13,16,19-hexaen-1-ol,

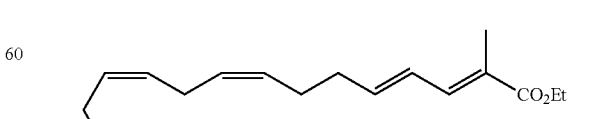

ethyl (2E,4E,8Z,11Z,14Z,17Z) 2-methyl-icosa-2,4,8,11,14,17-hexaenoate,

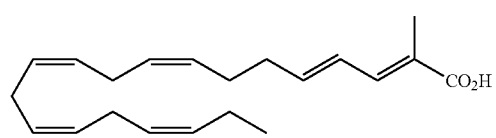

(2E,4E,8Z,11Z,14Z,17Z) 2-methyl-icosa-2,4,8,11,14,17-hexaenoic acid,

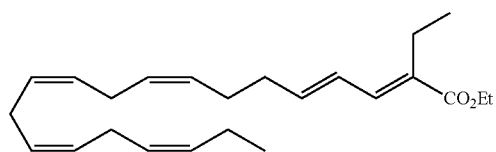

ethyl (2E,4E,8Z,11Z,14Z,17Z) 2-ethyl-icosa-2,4,8,11,14,17-hexaenoate,

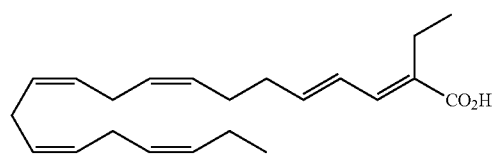

(2E,4E,8Z,11Z,14Z,17Z) 2-ethyl-icosa-2,4,8,11,14,17-hexaenoic acid,

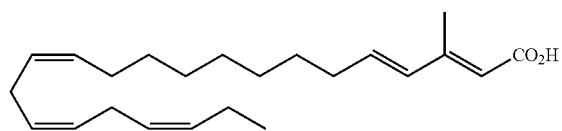

(2E,4E,13Z,16Z,19Z) 3-methyl-docosa-2,4,13,16,19-pentaenoic acid,

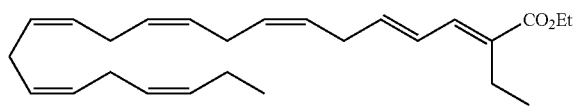

ethyl (2E,4E,7Z,10Z,13Z,16Z,19Z) 2-ethyl-docosa-2,4,7,10,13,16,19-heptaenoate,

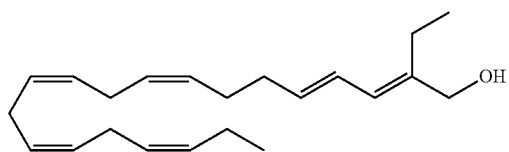

(2E,4E,8Z,11Z,14Z,17Z) 2-ethyl-icosa-2,4,8,11,14,17-hexaen-1-ol,

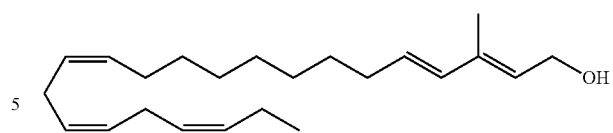

(2E,4E,13Z,16Z,19Z) 3-methyl-docosa-2,4,13,16,19-pentaen-1-ol,

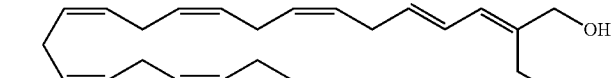

(2E,4E,7Z,10Z,13Z,16Z,19Z) 2-ethyl-docosa-2,4,7,10,13,16,19-heptaen-1-ol,

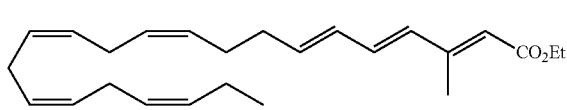

ethyl (2E,4E,6E,10Z,13Z,16Z,19Z) 3-methyl-docosa-2,4,6,10,13,16,19-heptaenoate, or

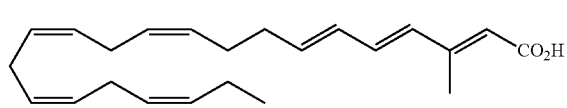

(2E,4E,6E,10Z,13Z,16Z,19Z) 3-methyl-docosa-2,4,6,10,13,16,19-heptaenoic acid.

21. The lipid compound according to claim 19, wherein when X is COR$_3$ and R$_3$ is hydroxy, X is a carboxylic acid derivative in the form of a triglyceride or a phospholipid.

22. A pharmaceutical composition comprising a compound according to claim 1.

23. The pharmaceutical composition according to claim 22, further comprising a pharmaceutically acceptable carrier, excipient, diluent, or any combination thereof.

24. The pharmaceutical composition according to claim 22 formulated for oral administration.

25. The pharmaceutical composition according to claim 22, formulated to provide a daily dosage ranging from 5 mg to 10 g of the lipid compound.

26. The pharmaceutical composition according to claim 25, formulated to provide a daily dosage ranging from 50 mg to 1 g of the lipid compound.

27. The pharmaceutical composition according to claim 25, formulated to provide a daily dosage ranging from 50 mg to 200 mg of the lipid compound.

28. A lipid composition comprising a lipid compound according to claim 1.

29. The lipid composition according to claim 28, wherein the lipid compound is present in an amount of at least 80% by weight of the lipid composition.

30. The lipid composition according to claim 29, wherein the lipid compound is present in an amount of at least 90% by weight of the lipid composition.

31. The lipid composition according to claim 29, wherein at the lipid compound is present in an amount of at least 95% by weight of the lipid composition.

32. The lipid composition according to claim 28, further comprising a pharmaceutically acceptable antioxidant.

33. The lipid composition according to claim 32, wherein said antioxidant is tocopherol.

34. A method for the production of a lipid compound according to claim 1, comprising reacting a compound chosen from

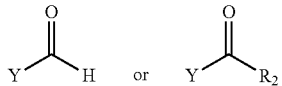

with either a phosphoryl-stabilized carbanion, which may be optionally substituted with $R_1$, or α-trimethylsilyl acetate, wherein $R_1$ and $R_2$ are the same or different and are chosen from a hydrogen atom, an alkyl group, a halogen atom, and an alkoxy group, and Y is a $C_9$ to $C_{21}$ unsubstituted alkene with at least one double bond having either E or Z configuration wherein $R_1$ and $R_2$ are not both a hydrogen atom.

* * * * *